US008212866B2

(12) United States Patent
Lemmer et al.

(10) Patent No.: US 8,212,866 B2
(45) Date of Patent: Jul. 3, 2012

(54) METHOD AND AN APPARATUS FOR LOCALIZATION OF SINGLE DYE MOLECULES IN THE FLUORESCENT MICROSCOPY

(75) Inventors: Paul Lemmer, Dossenheim (DE); Christoph Cremer, Heidelberg (DE); David Baddeley, Auckland (NZ); Heinz Eipel, Bensheim (DE)

(73) Assignee: Ruprecht-Karls-Universitat Heidelberg Kirchhoff-Institut fur Physik (DE)

( * ) Notice: Subject to any disclaimer, the term of this patent is extended or adjusted under 35 U.S.C. 154(b) by 644 days.

(21) Appl. No.: 12/404,488

(22) Filed: Mar. 16, 2009

(65) Prior Publication Data
US 2009/0237501 A1 Sep. 24, 2009

(30) Foreign Application Priority Data

Mar. 19, 2008 (DE) .......................... 10 2008 015 051
Nov. 14, 2008 (EP) .................. PCT/EP2008/009671

(51) Int. Cl.
*H04N 7/18* (2006.01)
(52) U.S. Cl. .............. 348/79; 348/78; 348/80; 340/692; 340/500; 340/506; 324/307; 324/309
(58) Field of Classification Search ..................... 248/79, 248/78, 80
See application file for complete search history.

(56) References Cited

U.S. PATENT DOCUMENTS

| 6,424,421 | B1 | 7/2002 | Cremer et al. |
| 7,109,459 | B2* | 9/2006 | Kam et al. .................. 250/201.4 |
| 7,342,717 | B1 | 3/2008 | Hausmann et al. |

| 2003/0207312 | A1* | 11/2003 | Sorge ................................ 435/6 |
| 2005/0121596 | A1* | 6/2005 | Kam et al. ................. 250/201.2 |
| 2008/0032414 | A1 | 2/2008 | Zhuang et al. |

FOREIGN PATENT DOCUMENTS

| DE | 297 01 663 | 4/1997 |
| DE | 198 30 596 | 1/1999 |
| DE | 100 52 823 | 5/2002 |
| WO | 03/031951 A1 | 4/2003 |
| WO | 2006/127692 A2 | 11/2006 |

OTHER PUBLICATIONS

Egner, A.; et al.: Fluorescience Nanoscopy in Whole Cells by Asynchronous Localization of Photswitching Emitters. In: Biophys. J., Nov. 2007, vol. 93, S. 328503290.
Gunkel, M.; et al.: Dual color localization microscopy of cellular nanostructures. In: Biotechnol. J, 2009, vol. 4, S. 927-938.
S.W. Hell, M Kroug, Ground-State-Depletion Fluorscence Microscopy: A Concept for Breaking the Diffraction Resolution Limit, applied Physics B 60, 495-497, Springer-Verlag (1995).

* cited by examiner

*Primary Examiner* — Jude Jean Gilles
(74) *Attorney, Agent, or Firm* — Gerald E. Hespos; Michael J. Porco

(57) ABSTRACT

A method and apparatus are provided for obtaining a sub-resolution spatial information of a sample labeled with at least one type fluorescent label. The sub-resolution spatial information has localization information about the positions of fluorescent molecules of the at least one type fluorescent label in at least one spatial direction. The method acquires localization image data by employing fluorescence localization microscopy. The acquired localization image data is processed to obtain the localization information about the positions of fluorescent molecules of the at least one type fluorescent label in at least one spatial direction. The step of processing includes determining in each of the detected images of the series the positions of the barycenters of the detected fluorescence emission distributions from the single fluorescent molecules of the one or more fluorescent labels in at least one spatial direction.

30 Claims, 10 Drawing Sheets

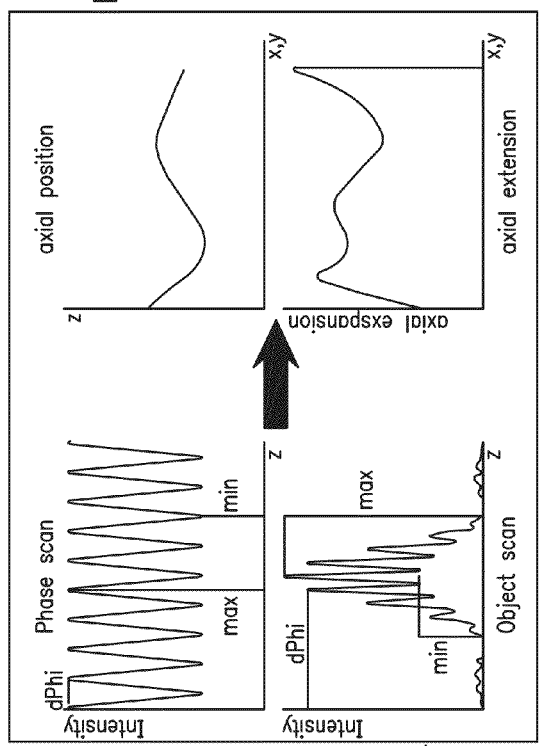

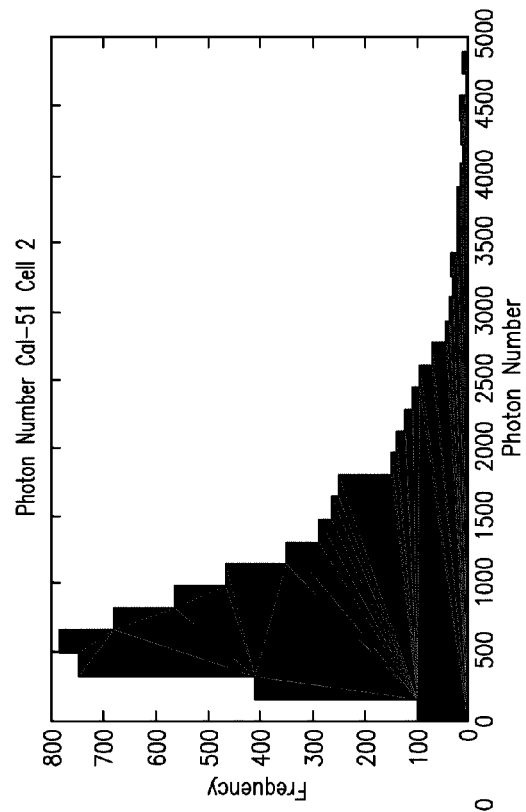
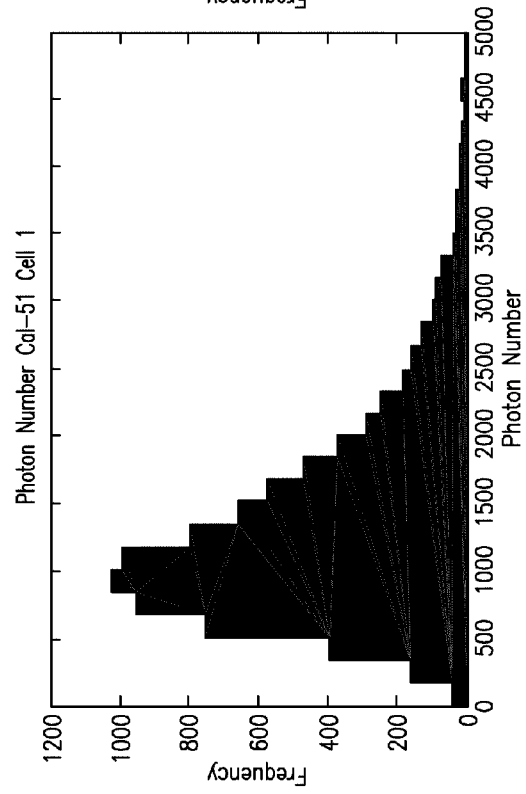

METHOD AND AN APPARATUS FOR LOCALIZATION OF SINGLE DYE MOLECULES IN THE FLUORESCENT MICROSCOPY

CROSS-REFERENCE TO RELATED APPLICATIONS

This application claims priority under 35 USC 119 on German Patent Appl. No. 10 2008 015 051.7 filed on Mar. 19, 2008 and further claims the benefit under 35 USC 120 based on International Appl. No. PCT/EP2008/009671 filed on Nov. 14, 2008. The disclosures of these two prior applications are incorporated herein by reference.

BACKGROUND OF THE INVENTION

1. Field of the Invention

The invention relates to an apparatus (a microscope, respectively a microscopic system) and a method for obtaining a sub-resolution spatial information of one or more objects in a region of interest of an observed sample. In particular, the invention relates to the detection and localization of fluorescence molecules employed to label the measured objects.

2. Description of the Related Art

It is known that due to the wave character of the light the images in light microscopy are diffraction limited. This is manifested in that point-like objects are registered as blurred (Airy-) discs in the image space on the sensor. The function describing this blurring is referred to as Point-Spread-Function or shortly PSF. If the relation between the maximal resolution of a microscope and the used numerical aperture of the objective (NA) and the wavelength (Lambda):

$$d\_min = Lambda/(2 \times NA),$$

which has been disclosed by Ernst Abbe (1873) is taken into account, one obtains a best resolution d_min of about 200 nm as the natural resolution limit when the best objectives and light in the visible region are used. Since numerous processes happen at a considerably smaller scale the overcoming of the Abbe-limit is one of the most difficult but the most important challenges in the modern light microscopy.

While Electron Microscopy and other ultrastructure imaging methods based on ionizing radiation have the great advantage of unprecedented resolution, "visible" light (i.e. light within the wavelength range of near ultraviolet to near infrared) offers other advantages, such as identification of multiple types of appropriately labeled molecules in single, three-dimensionally intact cells, and even in living ones. Thus, it is highly useful to complement the potential of ionizing radiation imaging procedures for the study of biological nanostructures with novel approaches to perform high resolution using visible light microscopy. Some examples of potential applications of this are in examining the nanostructure of cell membranes, or the genome structure of the cell nucleus.

For example, Fluorescence Energy Transfer (FRET) microscopy allows for example distance measurements between two molecule types down to the few nanometer level, using visible light for excitation. Fluorescence Correlation Spectroscopy or Fluorescence Recovery After Photobleaching (FRAP) make possible the analysis of intracellular mobilities or labeled, respectively marked molecules. For a full understanding of functional cellular processes, however, additional structural information is necessary. To solve these and many other important problems of cell biology and cellular biophysics, appropriate spatial analysis is indispensable.

A serious problem in achieving this goal is that conventional light optical resolution is limited to about 200 nm laterally and 600 nm axially, meaning that cellular nanostructures cannot be adequately resolved to provide full functional information.

Various recently introduced laseroptical "nanoscopy" approaches permit to overcome this problem, and to extend the spatial analysis far beyond the "Abbe/Rayleigh Limit" of optical resolution (here assumed to correspond in the object plane (x,y) to about half the wavelength used, according to the original formulas, and to about one wavelength in the direction of the optical axis (z)). In particular in the fluorescence microscopy it was possible, predominantly in the last ten years, to steadily increase the achievable resolution of the diffraction limited systems.

Thus for example in the concept of confocal laser scanning fluorescence 4Pi-microscopy the object is scanned by laser light focused from all sided ("4Pi geometry") and the fluorescence excited is detected "point-by-point". Using two opposing high numerical aperture lenses to concentrate two opposing laser beams constructively in a joint focus, confocal laser scanning 4Pi-microscopy has become an established "nanoscopy" method, allowing an axial optical resolution down to the 100 nm range. This is a resolution 5-7 times better than what can be achieved by conventional fluorescence microscopy methods.

In many imaging applications, the structural information desired is the size of nanostructures which are separated from each other by a distance larger than the Abbe limit. To solve this problem, Spatially Modulated Illumination (SMI) far field light microscopy was developed as one of the many possibilities for using structured illumination to improve spatial analysis. SMI microscopy is based on the creation of a standing wave field of laser light, which can be realized in various ways, such as by focusing coherent light into the back focal planes of two opposing objective lenses of high numerical aperture. The fluorescently labeled object is placed between the two lenses and moved axially in small steps (e.g. 20 nm or 40 nm) through the standing wave field. At each step, the emitted fluorescence is registered by a high sensitive CCD camera. This procedure allows axial diameter measurements of individual fluorescent subwavelength sized objects down to few tens of nanometers, and also the determination of axial distances between "point-like" fluorescent objects (at lateral distances larger than the Abbe limit) down to the range of a few tens of nanometers and with a precision in the 1 nm range. Several biophysical application examples indicate the usefulness of SMI-microscopy for the study of the size of transcription factories and of individual gene regions.

The employment of a structured lighting and a structured detection increases the resolution of a far-field and confocal methods at about factor of two laterally and up to a factor of six along the optical axis (axially). The methods for improving the lateral resolution are often simple to integrate in existing microscopes or to be newly implemented. In contrast the methods for maximal improvement of the axial resolution mostly employ technically most complex optical paths. For the analysis of living systems the lateral methods, which are often applied as far-field methods, are sufficiently fast. The predominantly confocal methods for improvement of the axial resolution are scanning techniques and are as such either too slow or do not fulfill the high optical requirements as such measurements.

Stimulated Emmision Depletion (STED) microscopy is a focused beam method, in which the size of the excited region is greatly reduced by stimulated emission depletion. Presently, this technique allows an optical lateral ((x,y)) resolution in the 15-20 nm range using visible light. In cases where the field of view can be made sufficiently small (in the few nanometer range), in vivo STED microscopy with tens of frames/second has been reported.

STED Microscopy can be regarded as a special case of RESOLFT (reversible saturable optical fluorescence transition microscopy), where in principal, optical resolution in the few nm range should become possible using visible light.

RESOLFT-methods offer through exploitation of non-linear effects theoretically arbitrary high resolution down to molecular scale. The success of these methods is, however, restricted by the physical properties of the used dyes, respectively markers or labels and the optical properties of the observed sample, respectively slide preparation. A three-dimensional object reconstruction had to rely up till now on quite complicated methods employing structured illumination. With the currently used dyes it was possible to achieve a lateral and axial improvement of the resolution, however those methods were up till now not appropriate for imagining of active processes.

Based on the experience that "point like" fluorescent objects can be light microscopically localized with a precision of more than one order of magnitude better than the diffraction limited resolution of conventional far field fluorescence light microscopy, Spectral Precision Distance Microscopy (SPDM) was conceived about a decade ago. SPDM is a far field light microscopy method based on:
 a) labelling of neighbouring "point like" objects with different spectral signatures (for abbreviation also called colors); and
 b) spectrally selective registration to "sort" the emitted photons according to their spectral signature; and
 c) high precision position monitoring.

Originally the "different spectral signatures" were realized by different excitation/emission spectra, but were conceived to include also other "photon sorting" modes like fluorescence life times, photoluminescence and stochastic labelling schemes to allow photophysical discrimination. In combination with fluorescence life time measurements, the application of the SPDM concept to nanometer resolution of single molecules was experimentally confirmed. In particular, using fluorescent labels of different photostable spectral signatures and procedures involving in situ calibration of chromatic shifts, a lateral (2D) position and distance resolution below 30 nm, and a three dimensional (3D) resolution below 50 nm was achieved in fixed cell nuclei after specific FISH labeling of small DNA targets using a standard confocal laser scanning microscope. Thus, SPDM was successfully applied to analyze the supramolecular architecture of genome regions in intact 3D conserved cell nuclei by position and distance measurements considerably below the conventional, diffraction limited optical resolution of high numerical aperture far field fluorescence microscopes. The SPDM concept (also called "colocalization") proved to be useful also in a variety of other applications, including single molecules.

During the first applications of the "SPDM" to biological nanostructure elucidation, the objects were labeled with fluorochrome molecules which had different emission wavelengths, and the signals were acquired synchronously. Fluorescence emission spectra of selectable molecules with typically 50 nm bandwidth are relatively broad. As such, in fluorescence microscopy, the detectable wavelengths are limited to a complete range of about 600 nm, and only a few "colors" (in the sense of variation in the emission spectra) can be used at the same time within the same object.

Since the original reports a number of conceptually related far field fluorescence methods have been proposed, for example BLINKING (meaning that the a light source emits light in pulses with a given frequency, much like the light houses); FPALM (fluorescence photoactivation localization microscopy), PALM (photoactivated localization microscopy), PALMIRA (PALM with independently running acquisition); STORM (stochastic optical reconstruction microscopy).

As a general denomination, all these approaches might be regarded as methods of "Spectrally Assigned Localization Microscopy" (SALM) where the localization of an object is assigned to a characteristic spectral signature. The underlying principle of these "SPDM/SALM" approaches is the "optical isolation" (in space and/or time domain) and hence independent localization of individual "point like" objects due to any photon based characteristics of the emitted light. This means that in a given diffraction limited observation volume defined for example by the (x,y, z) Full-Width-at-Half-Maxima (FWHM) of the Point-Spread-Function (PSF) of the microscope system used, at a given time interval and for a given spectral registration mode, only one such object (for example a singe molecule) or under certain conditions only few objects are registered.

By imaging fluorescent bursts of single molecules after light activation, the position of the molecules could be determined with a precision much higher than the full width at half maximum of the point spread function. In other words, these microscopy approaches are based on the registration of multiple (ex. thousands) of images of the same specimen, respectively same region of interest, so that the optical resolution is improved by "scanning" the fourth coordinate of the space-time continuum.

The molecules and proteins that are used for PALM and related techniques are fluorescent labels which are chemically modified (for example by adding appropriate side groups) in such a way that most of the fluorescent molecules are initially in an inactive state for the fluorescence excitation at a given wavelength $\lambda_{exc}$. This state (also called a "dark" spectral signature), can be changed to a fluorescent one (also called a "bright" spectral signature), for example by illumination with light of a defined wavelength $\lambda_{phot}$ (for example in the near ultraviolet), which is different from the one of fluorescence excitation. If the activation of the fluorescent markers, or in other words the transition form a "dark" spectral signature to a "bright" spectral signature, is done stochastically using low intensities, only few molecules within one acquisition time interval, respectively acquisition time frame of the detector are activated and thus an optical isolation of their signals may be achieved. Due to subsequent illumination with $\lambda_{exc}$, the fluorescent signal emitted by these optically isolated molecules ("bright" spectral signature) is then registered until they are irreversibly bleached (i.e. until an irreversible transition to a "dark" spectral signature). From these fluorescent signals, the position of the single molecules can be determined with high precision. Under good optical conditions, localization accuracy in the few nm-range is possible. Repetition of this procedure (for example by registration of about 10,000 individual image frames) allows one to obtain the positions of the individual molecules even if their mutual distances are far below the Abbe/Rayleigh-limit. The photoactivation process at $\lambda_{phot}$ and the use of a second laser line ($\lambda_{exc}$) can be avoided if an auto-activation of the molecules by a readout laser ($\lambda_{exc}$) is used.

The methods of the Spectrally Assigned Localization Microscopy (SALM)/Spectral-Precision-Distance Microscopy (shortly called thereafter localization microscopy) (DE 10052823.6, DE 29701663.3, U.S. Pat. No. 6,424,421, DE 19830596.6, U.S. Pat. No. 7,342,717, WO 2006/127692 A2, US 20080032414 A1) allow in principle a lateral resolution in a single-digit nanometer range. This localization microscopy is characterized in particular by the relatively low requirements concerning the needed optical and mechanical components. Also the adjustment of the apparatus is quite user-friendly. The localization microscopy uses for overcoming the Abbe-limit the fact, that one single fluorescent object can be almost arbitrary precisely localized. As described above, the precondition is that the diffraction limited disc corresponding to the fluorescence object is available spatially isolated, that is to say is not overlaid or superposed with other signals. The lateral position of the emitting molecule is generally determined from the center of the diffraction limited fluorescence disc. The precision with which such determination can be carried out is dependent on the number of the detected photons and on the related to it signal to noise ratio. Although the used sensors are typically two-dimensional sensor arrays, it is also possible to perform localization along the third space direction. Such localization requires, however, either very exact three-dimensional model functions of the point-spread-function (PSF) in combination with great number of the detected photons (>1000) or additional knowledge about the position of the observed molecule in the object space. To obtain such results is quite difficult using only methods of the pure localization microscopy, as disclosed for example in WO 2006/127692 A2. A method is also known that exploits astigmatism to empirically generate a three-dimensional point-spread-function, which is separated in axial and lateral portion and to fit this function to the collected data. The average precision, respectively accuracy with which the localization can be carried out is about 55 nm (23 nm standard deviation). This value represents a kind of natural limit for these methods due to the typical number of detected photons and the fact that the lens-PSF exhibits a higher blurring or smearing in axial direction. The pure localization microscopy with its single or multiple cyclic single point-reconstruction methods is ill-suited for the observation of active processes such as for example in vivo measurements of living cells. Accordingly it is always necessary to find a compromise between a sufficient number of detected photons and a realizable point density within one as small as possible time window. Also the mechanical stability of the microscope puts at very long detection times a further limit to the localization precision.

An object of the invention is to provide a method and an apparatus with which the limit of the localization precision, respectively accuracy of the up to now established localization microscopy can be overcome, while simultaneously accelerating and optimizing the localization process.

SUMMARY OF THE INVENTION

According to an aspect of the invention, there is provided a method for obtaining a sub-resolution spatial information of a sample labeled with at least one type fluorescent label, said sub-resolution spatial information comprising localization information about the positions of fluorescent molecules of the at least one type fluorescent label in at least one spatial direction, comprising the steps:
acquiring localization image data by employing fluorescence localization microscopy, wherein said localization image data comprises a series of images obtained by illuminating a region of interest of the sample with illumination light having intensity in the range of approximately 1 kW/cm$^2$ to approximately 1 MW/cm$^2$,
detecting by an information acquiring sensor of at least a portion of the fluorescent light emitted by at least a portion of the fluorescent molecules of the at least one type fluorescent label upon illumination, thereby obtaining an image of the region of interest;
repeating the steps of illuminating and detecting of the emitted fluorescent light a plurality of times, thereby obtaining the series of images, each image being taken at a different time step;
processing the acquired localization image data to thereby obtain said localization information about the positions of fluorescent molecules of the at least one type fluorescent label in at least one spatial direction, wherein the step of processing comprises determining in each of the detected images of the series the positions of the barycenters of the detected fluorescence emission distributions from the single fluorescent molecules of the one or more fluorescent labels in at least one spatial direction.

In particular, according to an aspect upon illumination with illumination light having intensity in the range of approximately 1 kW/cm$^2$ to 1 MW/cm$^2$, at least a portion of the fluorescent molecules are transferred from a first state to a second, state (which is distinct from the first state), emitting thereby fluorescent light.

The first state may be a fluorescent state. Here a 'fluorescent state' means in particular a conformation of the molecule where the absorption of photons results in the immediate (scale in the nanosecond range) emission of fluorescent photons.

The second state may be a semi-stable, or respectively semi-long lasting dark (for example a non-fluorescent) state. In particular, the second state may be a reversibly bleached state.

According to a further aspect, upon illumination, at least a portion of the fluorescent molecules of the at least one type fluorescent label are transferred from the first state to the second state and after recovery to the first state to a third, inactive state.

The third state may be a long lasting inactive (for example non-fluorescent or dark) state. In particular, the third state may be a irreversibly bleached state. The terms "fluorescent/non-fluorescent" used within the scope of the present invention refer generally to any states, which are spectrally distinguishable. In particular, the terms "fluorescent/non-fluorescent" may refer to different spectral ranges. Within the scope of the present invention the term "long lasting" refers to a time interval in the minutes to hours range and the term "semi-stable" or "semi-long lasting" refers to the state which exhibits stability within an interval from a millisecond to a minutes range.

The illumination may be carried out either continually or discontinually. In particular, the illuminating the one or more objects in the region of interest with illumination light having intensity in the range of approximately 1 kW/cm$^2$ to approximately 1 MW/cm$^2$ may be such that in a given diffraction limited observation volume and at a given time, statistically only one fluorescing molecule of a given fluorescent label type is present. Accordingly, each of the images acquired at each time step comprises a plurality of substantially spatially separated fluorescence signals from the single fluorescence molecules of the at least one type fluorescent label. The fluorescence signals from the single fluorescent molecules are detected by the information acquiring sensor generally in a form of fluorescence emission distributions. In addition, the employed intensity range allows for an efficient time separation of the single fluorescent signals from the fluorescent molecules.

From the obtained information about the spatial position of the barycenter of the fluorescence emission of the single fluorescent molecules of the one or more fluorescent labels, information about the spatial position of one or more fluorescently labeled objects within the sample, and/or the size of the one or more objects; and/or the distances between the objects in at least one spatial direction may be obtained.

According to an aspect of the present invention a new approach to achieving a resolution higher than the diffraction limited resolution (in the following sub-resolution) by using fluorescence localization microscopy is proposed. The term fluorescent "localization microscopy" used is intended to encompass in particular a Spectral Precision Distance Microscopy/Spectral Position Determination Microscopy (SPDM) or related microscopic techniques such as Spectrally assigned localization microscopy (SALM).

The intensity range of approximately 1 kW/cm$^2$ to approximately 1 MW/cm$^2$ has conventionally been considered as unsuitable for carrying out measurements with fluorescence localization microscopy. In particular, the intensity region of about 1 kW/cm$^2$ to 1 MW/cm$^2$ was believed to bring only drawbacks both for the wide field microscopy and for the confocal microscopy. Thus, it was believed that in the wide field microscopy the increasing of the intensity causes a considerably faster bleaching of the probe at no advantages for the achievable resolution. In the confocal microscopy it was considered that an additional intensity is required in order to achieve a better signal to noise ratio.

The present invention breaks with this conventional thought and proposes the use of high intensity illumination light for the purpose of fluorescent localization microscopy. In particular, it has been unexpectedly discovered that the use of high intensity illumination light in the range of 1 kW/cm$^2$ to 1 MW/cm$^2$ allows the achievement of better, respectively more efficient "optical isolation" (both spatially and temporarily) of the signals from the fluorescent molecules.

The use of localization microscopy, wherein the intensity of the illumination light is in the proposed intensity range, allows furthermore the employment of conventional, non-genetically modified proteins and other non-protein based fluorescent labels for sub-resolution measurements.

In addition, it becomes possible to efficiently combine localization microscopic measurements with other far or wide field measurements, so as to obtain additional spatial information, in particular additional spatial information in the direction perpendicular to the observed by localization microscopy object plane. This may lead to an increase of the axial resolution in comparison with conventional methods by a factor of about 30.

Further advantage is that the detection, respectively collection of data can be carried out relatively fast, for example within fewer than five minutes, which represents a difference of up to two orders in comparison to alternative methods requiring up to several hours. This is particularly advantageous for in-vivo observations in living systems. Thus, it is possible to avoid demanding and complicated technical solutions, which may counter or alleviate drift problems or provide for maintenance of life of the observed samples. In contrast, with the proposed method it is possible to carry out a meaningful in vivo observation also on the smallest structures.

Under the term "fluorescence" within the scope of the present application, it is to be understood any photon-interaction wherein there are differences between the illumination, respectively excitation spectrum, and the emission spectrum of the same object which cannot be explained based on the monochromatical absorption only. That includes for example in particular multiphoton interactions, by which the excitation wavelengths can be greater than the emission wavelengths. Thus the term fluorescence will be also used in the sense of this application for the closely related phenomena as "luminescence" and "photophosphorescence" or short "phosphorescence". This includes in particular the cases of longer fluorescence duration, for example in the millisecond range. The use of phosphorescent optical labels, respectively the use of phosphorescent molecules for optical labeling instead of fluorescent molecules may be for example advantageous in view of improving the in vivo applicability of the proposed new method, since these molecules allow for localization over a longer period of time.

Under the term "fluorescence molecule" within the scope of the present application, it is to be understood any "point-like" fluorescent element, that is to say any fluorescent element having size considerably smaller than the wavelength of the employed illumination, respectively excitation light), which is suitable for labeling of the measured sample.

The expression "different types of fluorescent labels" refers to fluorescent labels having different spectral signatures. In this context, "spectral signature" means any photo-physical property, such as for example fluorescent spectrum, absorption, lifetime, etc., which can be used for optically discriminated registration.

The partially cyclical process course in the localization microscopy can be described as follows:

It has been surprisingly found out, that, by illuminating fluorescently labelled specimens with illumination light having intensity within the interval of approximately 1 kW/cm$^2$ to approximately 1 MW/cm$^2$ the fluorescent molecules of almost any conventional fluorescent molecules (including organic fluorophores) are transferred to a fluorescent state and from there rapidly transferred to a semi-stable dark (non-fluorescent) state.

It was furthermore surprisingly found out, that from this semi-stable state, a portion of the dye molecules, which are used for the labeling, is activated and transferred again to a fluorescent state. The fluorescent molecules are thereby statistically, respectively stochastically activated, so that density of the activated molecules is lower than one molecule per diffraction limited detection volume. This volume can be well described with the help of the effective point-spread-function in that for example one counts all points with intensity higher than for example the half of the maximum intensity of the point-spread-function as belonging to the volume. After the activating an acquisition of the signal with the help of a sensor and subsequently the deactivating of the active molecules for example by means of bleaching and transferring to a long-lasting inactive state are carried out.

For the purposes of sub-resolution measurement, both the transfer from the fluorescent state to a semi-stable state (for example a reversibly bleached state) and the transfer from the fluorescent state to a semi-stable state and after recovery to the fluorescent state to another, long-lasting inactive state may be advantageously utilized. The first technique (transfer from a fluorescent state to a reversibly bleached state) may have advantages if fluorescent dyes or labels which either do not exhibit bleaching or exhibit low level of bleaching are employed. Such fluorescent dyes or labels are often used in the material testing or when quantum dots are employed. The effect of switching between a fluorescent state and a reversibly bleached state was also observed in ALexa 488 fluorescent label. Furthermore, in the first technique may be used to repeatedly detect a single molecule (similar to the STORM and dSTORM techniques).

The above described step of image detection, respectively acquisition is repeated multiple times and the acquired batch or stack of data taken at different times (so called timestack) is reconstructed by means of a computer implemented reconstruction process. For this purpose a segmentation of the data may be carried out initially to identify all molecules. In a further step a fitting of the employed two-dimensional or three-dimensional model functions for the point-spread-function to the identified signals may be carried out. The high intensity of illumination allows for the detection of the active molecules and their subsequent deactivation within a very short time period. This assures that the signals obtained from the single fluorescenting molecules are temporarily separated.

The obtained localization image data comprises thus a series of images of said region of interest taken at different time steps, each image comprising the detected and substantially spatially isolated fluorescent signals from the excited fluorescent molecules. If the employed information acquiring sensor is a two-dimensional sensor (for example a CCD-chip or other suitable two dimensional sensor, respectively sensor array), the acquired images are two dimensional images of the region of interest. Accordingly spatial information in two dimensions may be obtained. In an aspect the obtained images are images in an object plane. i.e. in a (x,y) plane substantially parallel to the optical axis of the employed localization microscope, wherein x and y are Cartesian coordinates in said object plane.

Depending on the live period of the semi-stable state, the integration time of the image acquiring sensor and/or the intensity of the illumination light may be adjusted, in order to achieve optimal temporal separation of the fluorescent signals. On the other hand, depending on the speed of image acquisition, respectively integration time of the information acquiring sensor it is possible to efficiently utilize semi-stable dark states with a stability period from ms range up to seconds and minutes range for the optical isolation of fluorescent signals upon the illumination with high intensity light.

It is also generally possible to extend the method to periods longer than periods in the minute range. In this case, it may be necessary, to employ further techniques to ensure the spatial stability of the fluorescent molecules used for labelling.

The obtained time series of (two-dimensional) images may be stored in an appropriate (three dimensional) data structure and subjected to a further processing, in order to obtain localization information about the positions of fluorescent molecules of the at least one type fluorescent label in at least one spatial direction, usually in at least two orthogonal spatial directions. In particular, by determining the barycenter, i.e. the center of gravity of the fluorescence emission of the single fluorescent molecules in each of the obtained two-dimensional images of the series, localization information about the spatial positions of the single fluorescent molecules of the employed one or more fluorescent labels (in the following also called fluorophores) in at least one spatial direction, usually at least in the object plane may be obtained. Different computer-implemented methods, such as for example fitting with an appropriate model function may be employed to this extend.

After registration of the positions of the fluorescent molecules through the whole localization image time series, all detected points, respectively all detected positions of the single fluorescent molecules may be assigned to one "merged" image, in particular to one "merged" two dimensional image comprising information about the spatial position and/or distances between the one or more fluorescent molecules of the employed fluorescent label (in the following also called fluorophore) in the region of interest, and in particular in the object plane.

From the localization information about the spatial position of the single fluorescent molecules used to label the one or more objects, one or more of the spatial position of the one or more fluorescently marked objects; and/or their size, respectively extension in at least one spatial direction; and/or the distances between the fluorescently labeled objects; and/or another spatial or topographical information may be determined with very high precision.

According to an aspect, the first state is a fluorescent state (an active state), the second state is a reversibly bleached state and the third state is an irreversibly bleached state.

Thus, the required optical isolation of the fluorescent signals is achieved by utilizing reversible photobleaching effect (also referred to as "blinking" or "flickering"). Unlike the usual bleaching effect used in PALM or FPALM, where the structure of the fluorescent molecules is irreversibly modified towards the non-fluorescent "dark" spectral signature state (at a given excitation conditions), the effect utilized by an aspect of the present invention is a reversible one.

In particular, it has been surprisingly found out that a great majority of the conventional fluorescent labels (including proteins or non-protein molecules) exhibit a reversibly bleached state, when illuminated with intensity light in the range of approximately 1 kW/cm$^2$ to approximately 1 MW/cm$^2$. The usual fluorescent state changes after typically several thousands emission cycles into an irreversibly bleached state, which is no longer available for the characteristic excitation. In addition, however, an additional reaction channel which leads to a reversibly bleached state becomes available to the fluorescent labels, respectively fluorescent molecules. The automatic recovery from this state occurs typically at time scales in the ms to minute range. Both the probability of a change, respectively a transition into this special state and the probability for regeneration from this special state can be strongly influenced, respectively controlled by means of illumination with a suitable light and/or a variation in the chemical environment (for example pH-value). According to an aspect of the invention the transition between the three distinct states—reversibly bleached, fluorescent and irreversibly bleached state—is utilized for the purposes of fluorescent localization microscopy. According to another aspect, the transition between two states—a fluorescent state and a reversibly bleached state is utilized for the purposes of fluorescent localization microscopy.

For an efficient execution, the transition probability for a reversible bleaching may be manipulated, respectively controlled, such that this transition becomes considerably more probable than the transition into an irreversibly bleached state. The object looses its fluorescence (transition into comparatively very long-lived reversible bleached state) and a low background is obtained. The molecules coming from the reversible bleached state are read out at suitably adjusted (typically high) laser intensity and converted, respectively transformed into an irreversible bleached state. This ensures that within one integration timeframe, respectively time-window of the information acquiring sensor (usually a CCD-chip, respectively camera) the critical molecule density of one molecule per diffraction limited volume is not surpassed. In this way a time, respectively temporal separation of the single signals may be achieved, which allows to efficiently apply the methods of the localization microscopy.

The method may furthermore comprise a step of labeling the one or more objects, so that the probability of a transition into a reversibly bleached state is higher than the probability of the transition into an irreversibly bleached state. The probability of the transition into a reversibly bleaches state may be influenced for example by the pH-value of the environment. Accordingly, the labeling the one or more objects may comprise controlling of the pH-value of the environment.

One possible way to describe the states of a fluorescent molecule at the existence of reversible bleaching is the following:

The functional connection between the three fundamental states of a molecule may be described by a transition:

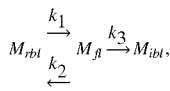

wherein:
$M_{rbl}$ is the reversibly bleached state,
$M_{fl}$ is the fluorescent state,
$M_{ibl}$ is the irreversibly bleached state of the molecule.

The rate constants of the crossing processes are indicated with $k_i$ (i=1, 2, 3), where the processes are assumed to be first order reactions. The ratio between the probabilities for the reversible and irreversible bleaching $$\frac{P_{rbl}}{P_{ibl}}$$

can be significantly affected by physiochemical modifications of the molecule due to its environment and/or due to illumination light with appropriate wavelength ("physiochemically modified fluorophores").

After starting to illuminate fluorescent molecules ($M_{fl}$) with excitation light, a certain amount (dependent on $P_{rbl}$) is bleached instantly

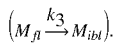

Another amount is transferred into reversible dark state

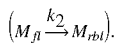

The transition between the fluorescent state and the reversibly bleached state upon illumination with light having high intensity may be used to achieve optical isolation in sub-resolution measurements.

The authors of the present invention envisaged that in addition to it, the statistical recovery of fluorescent molecules ("bright spectral signature") from the reversibly bleached state ($M_{rbl}$) and transition into an irreversibly bleached state of a "dark" spectral signature ($M_{ibl}$) with a delay time sufficient for a single fluorescent molecule registration, would allow an additional possibility for optical isolation of single molecules in the time domain. This offers a new approach to high resolution SPDM/SALM detection of the number and position of fluorescent molecules (even of the same type) within a given observation volume.

To realize an efficient sub-resolution localization, the condition has to be provided that within the integration time of the detector, the density of molecules with "bright" spectral signature ($M_{fl}$) is not higher than statistically one fluorescing molecule per diffraction limited observation volume. In addition, it is desirable to realized fast recovery and bleaching rates, since acquisition time is very critical factor in localization microscopy, due to the up to thousands of single image frames which may be required for a highly resolved SPDM/SALM image of a large number of molecules. To this extend, the light having intensity in the range of approximately 1 $kW/cm^2$ to approximately 1 $MW/cm^2$ (intensity range which has not been previously used, respectively has been avoided in the fluorescence microscopy) accelerates the readout and bleaching time.

The one or more fluorescent labels may be selected from one or more of the following groups:
  green fluorescent protein (GFP) and its derivates and/or modifications, for example green fluorescent protein (GFP), yellow fluorescent protein (YFP), cyan fluorescent protein (CFP), Orange Fluorescent Protein (OFP), enhanced green fluorescent protein (eGFP), modified GFP (emGFP), enhanced yellow fluorescent protein (eYFP);
  monomeric red fluorescent protein (mRFP) and its derivatives and/or modifications derivatives, for example mcherry; and/or
  rhodamin derivatives, for example Alexa- and/or attodyes; and/or
  coumarin derivatives; and/or
  xanthen derivatives, for example fluorescein; and/or
  cyanin derivatives.

In particular, the one or more fluorescent labels may comprise fluorescent proteins and their derivatives, for example cyan fluorescent protein (CFP), green fluorescent protein (GFP), yellow fluorescent protein (YFP), enhanced orange fluorescent protein (OFP), enhanced green fluorescent protein (eGFP), modified green fluorescent protein (emGFP), enhanced yellow fluorescent protein (eYFP) and/or monomeric red fluorescent protein (mRFP) and its derivatives and/or modifications derivatives, for example mCherry.

An important further factor which influences the precision of the localization microscopy is the used fluorescent labels themselves. Whereas fluorescent proteins are coexpressed with the protein, which is to be observed, and thus adhere directly to the structure, all other fluorescent molecules must be coupled or bound to the structure via specific linking molecules (for example antibodies or antigenes) or other chemical methods or processes. This coupling, respectively binding over usually greater distances often considerably limits the achievable localization precision, since the relative position of the molecule which emits the signal with respect to the structure under observation is afflicted with some blur or fuzziness. In addition the non-specific binding may cause significant problems, since the binding on the desired region is simply more probable than on some other position. In order to obtain a sufficiently strong signal, significantly more fluorescent molecules as actually needed may introduced into the sample under observation. When the objects to be observed relate to inner structures—for example within the cells—this causes a quite strong background, which needs to be dealt with. To overcome this problem is one of the most important objectives of the localization microscopy.

In order to obtain the best results fluorescent proteins or other structurally close molecules can be used as labels. New, genetically modified proteins, which do not exhibit fluorescence in a ground state, can be successively, for example photochemically, activated and localized, so that a point-wise reconstruction of the marked structure becomes possible.

These specially modified proteins must be introduced into the organism, respectively into the object to be observed, via molecular genetic techniques, which in particular in case of eukaryotic cells may be a tedious, expensive and complicated process.

On the other hand, convention fluorescent proteins, which nave not been genetically modified, have been known since the sixties years of the last century. Such proteins have been successfully and manifold employed and are often commercially available in stable expressed cell lines. A utilization of those fluorescent properties for localization microscopy was however up till now not conceivable.

Surprisingly, the employment of the illumination light with intensity in the range of about 1 kW/cm$^2$ to 1 MW/cm$^2$ allows the utilization of conventional, non-genetically modified fluorescent labels (for example fluorescent proteins and their derivatives such as CFP, GFP, YFP, eYFP, mRFP, etc.) as fluorescent labels for the purposes of sub-resolution fluorescent localization microscopy.

Such fluorescent labels are capable of reversible photobleaching when illuminated with illumination light having intensity in the range of approximately 1 kW/cm$^2$ to 1 MW/cm$^2$.

In particular, it has been found out that when illuminated with illumination light having intensity in the range of approximately 1 kW/cm$^2$ to 1 MW/cm$^2$ conventional fluorescent labels, respectively dyes (such as for example conventional fluorescent proteins) exhibit the effect of reversible photobleaching, which according to an aspect may be utilized in the localization microscopy. As already indicated above, the effect is pH-dependent and occurs on a time scale of 10 to 100 s, which can be modified under laser exposure.

With the help of the employed illumination with intensity in the range of about 1 kW/cm$^2$ to 1 MW/cm$^2$ the utilization of conventional fluorescent dyes and in particular conventional fluorescent proteins becomes as equally possible as the optimized activation of their specially modified relatives. Thus, also established stable labels and thousands of valuable slide preparations or specimens can be analyzed in a nanometer range with the help of the method according to an aspect of the present invention. Furthermore new fluorescence markers such as the so-called "smart-probes" can be utilized for the above described method. These markers are only active if they are bound to the designated structure and have thus changed their conformation. All of the remaining not bound and not washed away molecules remain thus invisible both for the applied wide field technique and for the localization microscopy. The main advantage is, thus, that disturbing background, which exists in the conventional methods, can be substantially eliminated. Furthermore exclusively the cells structure may be reconstructed.

In an aspect, the one or more fluorescent labels may comprise for example attodyes for non-proteins.

In a further aspect, the one or more fluorescent labels may comprise non-protein based fluorescent labels, in particular rhodamin derivatives, derivates, for example Alexa 488, Alexa 568 and/or Alexa 596.

In still further aspect, the one or more fluorescent labels may comprise xanthaen derivatives, for example fluorescein and its derivatives; and/or cianin derivatives.

In particular, it has been found out that the effect of reversible photobleaching is exhibited also in non-protein based fluorescent labels, such as for example fluorescein derivates (e.g. Alexa 488, Alexa 568 and/or Alexa 596.)

As indicated above other protein or non-protein based fluorescent labels may be also efficiently utilized.

Accordingly, in the following any fluorescent label (i.e. both protein based and non-protein based fluorescent labels) of this family of excitation activated, reversible photobleaching fluorophores will be called in the following physically modifiable fluorophores (PHYMOD-fluorophores).

The employed fluorescence localization microscope may have a far field set-up of the optical illumination path, In particular, the fluorescence localization microscope may have a confocal set-up of the optical illumination path, a wide field set-up of the optical illumination path, a 4Pi set-up, a STED set-up or STED-4Pi set-up. The detection path may have a wide field arrangement or set-up. In particular, the information acquiring sensor may be a two-dimensional sensor array capable of obtaining two-dimensional images of the region of observation.

The principle of illumination of fluorescently marked objects with light having high intensity and the subsequent detection of the fluorescent light as described above may be applied for microscopic observations employing a variety of optical set-ups of the illumination path.

In particular by introducing slight modifications it is possible to adapt the already existing conventional confocal microscopes for sub-resolution measurements, for example sub-resolution measurements in the nanometer range. Such slight modifications may be for example the introduction of an additional lens, and/or the employing of a two-dimensional sensor array (for example a CCD camera) for image acquisition; and/or minor modifications of the software for control of ray positioning and/or focusing. For example a confocal illumination may be employed in a two-photon modus, in order to carry out observations outside of the region of interest.

In a microscope with a confocal set-up of the optical illumination path generally a small region of interest having a diameter from about 200 nm (such as for example in case of diffraction limited focusing) to about 1 µm (such as for example in case of slight defocusing) may be illuminated with illumination light (usually a laser light) having intensity in the range of about 1 kW/cm$^2$ to about 1 MW/cm$^2$. The fluorescence emitted from the fluorescently marked object may be detected by a two-dimensional image sensor (for example a CCD camera). The center of the fluorescence emission may be then localized using suitable image processing algorithms, for example the algorithms described in more detail below. After completing the measuring (for example the SPDM measurement) at a given region of interest, the illumination light may be directed at another region of interest and the measurement repeated. The above procedures may be repeated until the whole object is scanned.

In comparison with a wide field illumination, the illuminated region of interest in a microscope having a confocal set-up of the optical illumination path may be considerably smaller. For example, in a microscope having a confocal illumination set-up the focal point has a surface of about 0.1 µm$^2$ (i.e. about 0.3 µm×0.3 µm) as compared to a surface of up to about 100×100 µm$^2$, which is usually illuminated in a microscope having a wide field illumination set-up. Thus, in a microscope having a confocal set-up of the optical illumination path the output laser power necessary for illumination of the region of interest with the required high intensity light may be generally up to several orders of magnitude less than the output laser power necessary for illumination of the region of interest in microscope having a wide field set-up of the optical illumination path.

Accordingly, in a microscope having a confocal set-up of the optical illumination path it is possible to employ lasers having relatively low output power lasers for illumination.

Furthermore, it is also possible to employ dyes, which are not easily excitable under wide field illumination for fluorescently marking of the objects. In addition, since in a confocal microscope only small selected areas are illuminated at a time, the total energy $E_{tot}$ absorbed by a measured object (for example a cell) at a given Intensity I of the illumination light is considerably less than the total energy absorbed in case of wide field illumination. This may be illustrated by the following example:

The total energy may be calculated by the formula:

$$E_{tot}=k*I*S*t,$$

wherein $k \leq 1$ is a constant, which describes the absorption;
I is the intensity of the illumination light;
S is the illuminated surface area; and
t is the illumination time.

In case of wide field illumination, the illuminated surface area may be for example about $10 \times 10$ μm². The total energy absorbed by the measured object is then:

$$E_{tot} \approx k*I*100*t=I*t*100 \text{ energy units.}$$

In case of confocal illumination the illuminated surface area may be about 0.1 μm². The number of selected clusters may be 10, so that the total illumination time is multiplied by 10. The total energy absorbed by the measured object is then:

$$E_{tot} \approx I*0.1*10*t=I*t*1 \text{ energy units.}$$

In other words, in case of confocal illumination the total absorbed energy is considerably less than in case of wide, respectively wide field illumination. Furthermore, energy is absorbed over longer period of time. This may be of importance in view of minimizing the photon induced damages (for example in case of in-vivo measurements).

Applications of microscopes having confocal set-up of the optical illumination path may be for example the measurements of selected protein complexes clusters in a single cell (membrane protein clusters, nuclear pore complexes, etc.). The selection may be carried out for example by means of a conventional epi-fluorescence microscope or confocal laser scanning microscopy.

The employed fluorescence localization microscope may have other various modes of Point Spread Function Engineering and Structured/Patterned Illumination Schemes. In this case the combination with the above described localization microscopy method may result in considerably shorter detecting, respectively recording time.

In particular, one possible realization of a wide field optical set-up may comprise two objective lenses with a common optical axis, arranged such that a standing wave field is formed along the optical axis by the interference of two counter propagating collimated beams, focused in the back focal planes of the two objective lenses. The sample to be observed is positioned within the standing wave field. This optical set-up allows for an efficient integration with further wide field methods employing structured illumination light, in particular spatially modulated illumination light, as will be described below in more detail.

With a wide field optical set-up a two dimensional information acquisition sensor may acquire at each time step a two dimensional images of the illuminated region of interest in the (x,y) object plane, which is generally perpendicular to the optical axis of the wide field microscope. Accordingly, lateral spatial information about the spatial position of the one or more fluorescently labeled objects; and/or their sizes; and/or the distances between the objects in the (x,y) plane may be obtained.

The used illumination light, respectively optical radiation may be monochromatic. Thus, it is possible to use one single wave length for the whole measurement, respectively analysis process. The localization microscopy is carried out thereby within the intensity range of about 1 kW/cm² to 1 MW/cm². This brings economical and technical advantages over conventional systems, which employ solely localization microscopy and which employ at least two wave lengths for the activating, excitation and deactivating of the dye molecules. The number of parameters which must be varied can be thus reduced at least in half. Naturally the employment of more than one wave length is also in accordance with the invention. This can be for example advantageous if the localization of multiple molecule types is aimed at.

Alternatively, a plurality of different types of fluorescent labels may be employed and the step of acquiring localization image data of one or more objects in a region of interest by employing fluorescence localization microscopy may be carried out separately for each fluorescent label using illumination light with an optimal intensity selected from within the range of about 1 kW/cm² to about 1 MW/cm².

This allows the achievement of a maximal localization precision and of a maximal number of localized fluorescent molecules. In particular, by determining a molecule-specific optimal illumination within the intensity range of about 1 kW/cm² to 1 MW/cm² it is possible to optimize the localization precision and the number of the localized molecules and thus the reconstruction Since the localization precision and the number of the localized molecules often cannot be simultaneously maximized it may be necessary to make a compromise.

Several computer implemented algorithms may be utilized to extract spatial data from the acquired image series. Thus for example, a Gaussian model function (optionally taking into account any background subtraction) may be fitted to the obtained raw or preprocessed localization image data. Another example is the performing of non-liner fit based on the Levenberg Marquard algorithm using an analytically calculated point spread function. The latter method allows to further obtain an estimation of the localization precision.

According to an aspect the step of processing the acquired localization image data comprises fitting of a model function f(x,y) to the acquired fluorescent emission distributions from the single fluorescent molecules in each of the two dimensional images of the time series:

$$f(x, y) = A\exp\left(-\frac{(x_0 - x)^2 + (y_0 - y)^2}{2\sigma^2}\right) + B_0 + B_1(x_0 - x) + B_2(y_0 - y),$$

wherein
x and y are Cartesian coordinates in an object plane, perpendicular to the optical axis of the microscope;
$x_0$ and $y_0$ are the starting parameters for the position, which are determined as the center of the segmented signal;
A is the amplitude of the distribution, and
$B_0$, $B_1$, $B_2$ are parameters describing linear background.

Prior to performing the fitting step, the individual fluorescent signals from the fluorescent molecules may be detected along the acquired image series by performing a division of each two subsequent images in the acquired time series of images. This allows the detection of local intensity differences and facilitates the elimination of the background noise. The fitting takes then into account the background subtraction.

After registration of positions of the fluorescent molecules through the whole localization image data time series, all detected points may be assigned to one "merged" image, in particular one merged two-dimensional image. Position and/or distance measurements may be obtained from the barycenter distances between these reconstructed points taking into account the localization precision. The reconstructed points are generally spread by a Gaussian intensity distribution with a standard deviation equal to the mean localization precision of the respective fluorescent molecules.

According to another aspect, the detected signals (i.e. the detected image data) may be decomposed in its characteristic components or vectors (for example by means of Fourier transformation or other transformations). In order to determine the contribution of each component, respectively vector, the image data may be cross correlated with the corresponding vector. For the segmenting step it is then possible to consider only sampled data (i.e. pixels) with significant amplitude. By means of linear combinations of different vectors, is possible to carry out different classifications of the detected signals.

According to a further aspect, in the step of acquiring localization image data the one or more objects in the region of interest are illuminated by a structured illumination light.

The structured illumination light may be a suitably spatially structured, respectively patterned illumination light, in particular an illumination light, which is a suitably spatially structured or modulated in the (x, y) object plane, i.e. plane perpendicular to the optical axis of the localization microscope. Either the object (object scan) or the phase (phase scan) of the illumination may be moved between two detected image frames, i.e. between two image acquisitions. It is also possible to combine both techniques.

As disclosed in DE 19830596.6, JP 2000502406, U.S. Ser. No. 09/462,435, PCT/EP 02/11343 and WO 2006/127692 A2 the localization precision can be further increased if a structured illumination is also employed for the localization microscopy. The illumination may be thereby stationary during the signal acquisition and the fact is exploited that additional information about the potential location of the detected single molecule is obtained, since the fluorescent molecules are preferably located in a region with a higher intensity.

According to an aspect, a (spatially) structured, respectively modulated illumination, which is moved during the excitation of at least one dye molecule, may be used. The phase of the modulation is in this case reconstructed in the detected signal from the fluorescence molecules. This enables the determination of the position of at least one molecule associated with the signal relative to at least one fluorescent reference point to be determined with maximal under these condition precision.

One advantage of the movement of the structured illumination during the signal acquisition is that the single molecules can be localized with a maximal under these circumstances precision. It is thereby exploited, that the relative position of the fluorescent molecules to each other or with respect to an additional labeling can be determined from the obtained phase information. The precision with which the phase can be determined lies within a single-digit nanometer range. This precision differs in about one order of magnitude from the conventionally achievable under these circumstances localization precision.

Although in various SPDM/SALM methods a lateral (x,y) localization of single molecules (i.e. in object plane perpendicular to the optical axis) can be successfully performed, the localization along the optical axis (z) has proved to be challenging. To obtain a three dimensional reconstruction of labeled objects (i.e. the x, y, z coordinates of the fluorescently labeled molecules) various approaches can be used. One possible solution is to use confocal laser scanning or confocal laser scanning 4Pi microscopy to obtain the three dimensional positions of the objects.

Another possibility is to use the three dimensional information within the laterally acquired signal. Since all light emitting (i.e. fluorescenting) molecules are "point-like" (i.e. have size considerably smaller than the wavelength of the illumination light), one can assume that they all are imaged in the same way (disregarding spatial orientation effects of the molecules as producing aberrations in the 1 nm range under the conditions used).

The fact that out-of focus objects appear more blurred, and that the Point Spread Function (PSF) is not symmetric along the optical axis can also be used to localize photon emitting sources in all spatial dimensions. If the propagation path of the electromagnetic waves is well known, under else ideal registration conditions the accuracy of the axial localization (i.e. along the optical axis) is restricted only be the number of photons detected, analogous to the lateral localization (i.e. in the object plane (x, y)). Using common photoactivatable or photoswitchable flurophores in combination with biplane detection or a systematically modified PSF, a 3D localization accuracy of about 60 to 80 nm FWHM can be achieved.

According to an aspect, the localization microscopy measurements are combined with far, respectively wide field microscopical measurements employing spatially structured or modulated illumination.

Thus, in an aspect the method may further comprise acquiring additional wide field image data comprising a series of wide field images of the region of interest by employing a wide field fluorescence microscopy using illumination light, which is spatially structured, respectively modulated along an optical axis of the microscope, said acquiring additional wide field image data being obtained by:
  illuminating the one or more objects in the region of interest with the structured illumination light;
  detecting a wide field image of the fluorescent light emitted from the fluorescent molecules of the one or more fluorescent labels;
  moving the object and/or the structured illumination light in discrete steps along the optical axis and detecting at each step a wide field image of the fluorescent light emitted from the fluorescent molecules, thereby obtaining said series of wide field images of the region of interest,
wherein said step of acquiring additional wide field image data of the one or more objects is carried out before the step of acquiring localization image data.

The method may further comprise the step of processing the acquired additional wide field image data to obtain additional spatial information comprising information about the spatial extension along the optical axis of at least one fluorescently labeled object in the sample and/or additional spatial information of the positions of the barycenters of the detected fluorescence emission distribution of the single fluorescent molecules in the direction of the optical axis. The localization information obtained by the localization microscopy may be combined with the additional spatial information obtained by the wide field fluorescence microscopy using structured illumination light.

One of the advantages of the above approaches is that it is possible to overcome the limit for the localization precision or accuracy along the optical axis at otherwise identical conditions of the localization-microscopical observation. Depending on the art, respectively type of the structural illumination it is possible to determine with a precision of up to few nanometers the size of the fluorescently marked object structures, which exhibit smaller extension, respectively size than the distance between the maxima of the intensity in the structured illumination. The same applies also to the position of the center, respectively barycenter of the labeling. Since with a localization microscopy one is primarily interested in very small structures, it is known immediately after one lateral detection and localization of the signal in which "depth" (barycenter of the labeling) the molecule must be lying and with which precision its position was determined (extension of the object). In this way it is possible to carry out three-dimensional single molecular localizations with an absolute precision (no standard deviation) of under 40 nm in axial and under 10 nm (about 4 nm standard deviation) in lateral direction even at quite poor photon yields.

Another advantage is that the combined method employing both localization microscopy and wide field fluorescent microscopy using spatially structured illumination light is considerably less dependent on the photon statistics of the single fluorescent molecules used for labeling, since always a great number of molecules are simultaneously contributing to the signal. A combined method according to an aspect of the invention may increase the axial localization precision by factor of 30 in comparison with conventional methods.

The illumination light may be spatially structured, respectively patterned in a number of different ways. In particular, the structured illumination light may be an illumination light spatially structured or modulated along at least the optical axis of the employed (wide field) microscope. An example of such illumination light, which is spatially structured along the optical axis is for example the standing wave field formed by an interference of two counter propagating laser beams. This can be achieved for example by focusing two beams emitted from the same laser source into the back focal planes of two opposing high numerical aperture objective lenses. The fluorescence labeled objects, respectively object structures positioned in the standing wave field, respectively in the structured illumination field are excited according to their position. The relevant image data may be obtained either by moving the object in the static structured illumination (object scan), by moving the structured illumination, while the object remains static (phase scan) or by a combination of both methods. Information concerning the spatial extension along the optical axis of at least one fluorescently labeled object in the sample and/or additional spatial information of the positions of the barycenters of the detected fluorescence emission distribution of the single fluorescent molecules in the direction the optical axis may be obtained from the intensity profile along the optical axis.

According to an aspect wide field observation, respectively measurement of the object can be carried out in advance. This allows making of some important conclusions or assertions about the object itself before the object is reconstructed with the localization microscopy. Thus it is possible for example to estimate in advance how well the labeling has been carried out. Crude or relatively great changes in the structure such as for example current or flow processes can be measured in vivo.

The detection, respectively collection of data according to an aspect can be carried out within fewer than five minutes, which represents a difference of up to two orders in comparison to alternative methods requiring up to several hours. This is particularly advantageous for in-vivo observations in living systems. Thus, it is possible to avoid demanding and complicated technical solutions, which may counter or alleviate drift problems or provide for maintenance of life of the observed samples. In contrast, with the proposed method it is possible to carry out a meaningful in vivo observation also on the smallest structures.

The wide field measurements using structured illumination light, in particular spatially modulated illumination light along an optical axis of the microscopic system may be carried out by illuminating with light intensities under 1 $kW/cm^2$.

The processing of the obtained data may comprise:
generating a common theoretical three dimensional model function for all detected signals within the one or more objects, wherein said three dimensional model function is divided in plurality of two dimensional layers along the optical axis, and
performing a lateral cross correlation of the acquired three dimensional image data and said three dimensional model function, wherein the maxima of the correlation function represent both one object identification and one three-dimensional localization.

The three dimensional model function may be for example a three dimensional model of the point spread function. The three dimensional lateral correlation (only two of the three possible integrations are carried out) may be performed according to the established mathematical principles, wherein each layer of the three dimensional point spread function with each image layer. Thus for example it is possible to obtain the lateral and the axial amplitude maxima, which carry information about both the lateral position (pixel with high amplitude) and the axial position (layer with highest amplitude) of the fluorescent molecule, respectively fluorescently labeled object.

The three-dimensional model function may be for example divided in "n" two-dimensional layers. The three dimensional image data are obtained by combining "n" copies of a single two-dimensional image from the obtained series of wide field images to a three-dimensional data stack. The same operation (i.e. the lateral cross-correlation is carried out for all images of the obtained time series of wide field images.

It is also possible to generate a common two-dimensional model function and to perform a lateral cross correlation of the model function with each two-dimensional image from the obtained series of wide field images.

The above described methods are also applicable to the image data obtained by means of fluorescent localization microscopy. In particular, the cross-correlation method can be also applied for sets of images obtained without the use of structured illumination. In this case, the volume, respectively three dimensional information of the point spread function is locally "compared" with the image data. It is thus possible not only to combine the segmentation and localization processes but also to dispense with a relatively computationally intensive fitting of the model function via fit-algorithms such as Levenberg-Marquardt or other modified leased-squares-algorithms. In particular, the segmenting may be carried out by applying a threshold method, wherein significantly higher amplitudes are assigned to the cross-correlation objects. The localization of each object is carried out—as explained above—by evaluating the amplitude in the segmented region.

The reconstruction method according to this aspect of the invention is characterized in particular in that it utilizes the fact that all detected signals from the dye molecules are emitted within a single small structure. In such case it is possible to disregard the disturbing differences in the refraction index of the environment, respectively surroundings. One single three-dimensional model function is thereby generated and for example cross-correlated with the acquired data batch, respectively data stack as explained above.

In the resulting stack it is possible to immediately carry out an identification of the single molecules and simultaneously the position of each molecule in the object or image space from the occurring maxima which describe the similarity of the model function to the signal in one particular layer. Thus for example, information about the position in the object or image space may be obtained by analyzing the position of the maximum of the intensity.

A threshold method may be applied to the obtained correlation maxima. The threshold method may be used for optimizing of the object identification and the 3D-localization of the fluorescent dye molecules a threshold method. In particular, the threshold-analysis method can be used to optimize the reconstruction method by evaluating only significant maxima. Thus, additional means for quality control of the reconstruction may be obtained.

Instead of a cross-correlation a wavelet correlation or similar methods may be used.

The method may further comprise a step of a spatial calibration of the structured illumination, wherein the spatial calibration carried out with the help of at least one fluorescent reference point.

According to a further aspect a spatial calibration of the structured illumination may be carried out with the help of at least one fluorescent reference point. By using a calibration method and the employment of at least one fluorescent reference point, with the aid of which the location, respectively position and the intensity of the standing-wave field can be directly measured and oriented, it is possible to optimize the utilization of the structured illumination and/or to describe the structured illumination with maximal precision. As a reference point, a thin, weakly fluorescenting layer on the coverglass of the coverslip, respectively sample preparation, such as for example layer of photo-lacquer, respectively photoresist, may be employed.

According to an aspect during the step of acquiring additional image data of said one or more objects with wide field fluorescence microscopy using structured illumination light, the one or more objects are illuminated with the structured illumination such, that at least a portion of the fluorescence molecules of the at least one fluorescent label is transferred in an active state and is used for the corresponding wide field observation, whereas a second portion of the fluorescence molecules remains in an inactive state. During the step of acquiring localization image data by employing fluorescence localization microscopy a second portion of the fluorescence molecules is activated by changing of the illumination light intensity of the optical radiation to the one lying within the range of about 1 kW/cm$^2$ to about 1 MW/cm$^2$, wherein said step of acquiring localization image data by employing fluorescence localization microscopy is carried out on the basis of the second part of the fluorescent molecules. The above mentioned active state may be a fluorescent state, and the above mentioned inactive state may be a non-fluorescent state, for example reversible bleached state or an irreversible bleached state. In particularly, in an active state, the fluorophor (or fluorescent molecule) is capable of emitting a characteristic radiation in a given spectral range (which is detectable by the imaging system) upon excitation. In an inactive state the fluorophor does not exhibit any detectable emission. The inactive states may be generally divided into "reversible" and "irreversible" depending on their life span.

Accordingly, it is possible to use initially inactive fluorescent molecules for the wide field measurements, if a sufficient portion of these molecules is activated for the purpose of the wide field observation. The partial activating of the molecules for the purpose of the wide field observation can be carried out for example with a second illumination wavelength. Different activating methods, such as for example thermal activation, can be also employed. The second portion of the dye molecules is employed for the subsequent localization in the localization microscopy. It is also possible to label the objects with a multiple labels comprising more than one types of dye, respectively dye molecules, so that one type can be used for the wide field observation and the other for the subsequent single molecule localization in the localization microscopy.

A further aspect of the invention relates to a fluorescence localization microscope for obtaining a sub-resolution spatial information of a sample labeled with at least one type fluorescent label, said sub-resolution spatial information comprising localization information about the positions of fluorescent molecules of the at least one type fluorescent label in at least one spatial direction, said microscope comprising:
  an illumination optics defining an optical illumination path, configured to illuminate the one or more objects in a region of interest;
  at least one additional optical element positioned within the optical illumination path of the localization microscope, the at least one additional optical element configured to enable a switching of the intensity of the illumination light to an intensity lying within the range of 1 kW/cm$^2$ to 1 MW/cm$^2$ and/or an adjustment, respectively regulation of the intensity of the illumination light within the range of 1 kW/cm$^2$ to 1 MW/cm$^2$;
  at least one information acquiring sensor positioned in an optical detection path, configured to detect at least a portion of the fluorescent light emitted by at least a portion of the fluorescent molecules of the at least one type fluorescent label upon illumination, thereby obtaining an image of the illuminated region of interest.

As already explained above, according to an aspect upon illumination with illumination light having intensity in the range of approximately 1 kW/cm$^2$ to 1 MW/cm$^2$, at least a portion of the fluorescent molecules are transferred from a first (fluorescent) state to a second semi-stable (for example reversibly bleached state).

According to a further aspect, upon illumination, at least a portion of the fluorescent molecules of the at least one type fluorescent label are transferred from the first state to the second state and after recovery to the first state to a third, long-lasting inactive state (for example an irreversibly bleached state).

The information acquiring sensor may be a two-dimensional sensor (for example a CCD-chip or other suitable two dimensional sensor, respectively sensor array), the acquired images are two dimensional images of the region of interest. Accordingly spatial information in two dimensions may be obtained. In an aspect the obtained images are images in an object plane. i.e. in a (x,y) plane substantially parallel to the optical axis of the employed localization microscope, wherein x and y are Cartesian coordinates in said object plane.

The microscope may further comprise a storing means (for example memory) for storing the image detected by the information acquiring sensor. In an aspect the storing means is configured to store a plurality, respectively a series of images detected by the information acquiring sensor at different type steps by repeatedly illuminating the sample and detecting the fluorescent light emitted from the fluorescent molecules. The series of images may be stored in an appropriate data structure, for example a three dimensional data stack comprising a plurality of two dimensional images.

The microscope may further comprise one or more illumination sources, for example one or more lasers. In an aspect the illumination light may be suitably spatially structured, respectively modulated in at least one spatial direction, in particular along the optical axis of the microscope. Accordingly, the microscope may further comprise means for spatially structuring, respectively modulating the illumination light in at least one spatial direction. An example of a suitably spatially structured, respectively modulated light along the optical axis is the standing wave, respectively illumination field formed by the interference of two counter propagating light beams. Such standing wave field may be for example formed by focusing two beams emitted from the same light source in the back focal planes of two opposing objective lenses having high numerical apertures. Further relatively low price realizations of a structured illumination can be for example by means of one or more optical gratings by means of a multiray interference.

In an aspect very low price laser pointers may be employed as illumination sources. This enables the realization of a fully functional wide field localization microscopic set-up optionally with some type of structured illumination integrated into it for a relatively low price. Even without employment of expensive special objectives, main frame or large capacity computers and special sensors the imaging power of such systems within an acceptable time period of under one hour may be better than that of conventionally obtainable microscopic systems. In addition, the fact that in the simplest case there is only one degree of freedom available to a user for manipulation (intensity control for example via lens position) assures that such apparatus can be used by everybody even without further knowledge in the field of optic, mechanic or electronic.

The localization microscope may have a confocal set-up of the optical illumination path, a wide field set-up of the optical illumination path, a 4Pi set-up, a STED set-up or STED-4Pi set-up or other modes of Point Spread Function Engineering and Structured/Patterned Illumination Schemes. The detection path may have a wide field arrangement. In particular, the information acquiring sensor may be a two-dimensional sensor array capable of obtaining two-dimensional images of the region of observation.

According to an aspect a conventional wide field illumination can be easily modified by the employment of at least one suitable optical element so as to enable the switching and/or the adjustment of the intensity of the optical radiation, respectively illumination light to an intensity lying within the intensity range of 1 kW/cm$^2$ to 1 MW/cm$^2$. Thus the methods according to any of the aspects of the invention can be enabled, respectively facilitated. With certain dyes or markers it can be advantageous to extend this intensity interval or window in the direction of the higher or lower values.

The at least one additional optical element may comprise one or more of
  at least one lens or a lens system;
  at least one gray filter or a gray filter set;
  at least one polarization filter;
  at least one acoustooptical modulator; and/or
  at least one electrooptical modulator.

Particularly easy to implement in a microscope are for example a single lens or a lens system or a single gray filter or a gray filter set. A polarization filter or a set of polarization filters may provide a convenient alternative for continuously adjusting or regulating the intensity of the illumination with polarized light sources.

Acousto-optical or electro-optical modulators according represent still another alternative. Similarly, it is possible to implement a combination of the above elements, for example a combination from a single lens and a gray filter set.

The microscope may further comprise at least one additional sensor, which is used in at least one additional optical detection path, said additional sensor and said additional optical detection path configured to register at least a portion of the fluorescent light, which does not reach the information acquiring sensor.

At least one second additional optical element may be positioned in the least one additional optical detection path.

The microscope may comprise furthermore a processing unit, configured to process the acquired localization image data to obtain sub-resolution spatial information of a sample labeled with at least one type fluorescent label, said sub-resolution spatial information comprising localization information about the positions of fluorescent molecules of the at least one type fluorescent label in at least one spatial direction. In particular the processing unit may be configured to determine in each of the detected images of the series the positions of the barycenters of the detected fluorescence emission distributions from the single fluorescent molecules of the one or more fluorescent labels in at least one spatial direction.

The processing unit may be further configured to process the localization information about the positions of fluorescent molecules of the at least one type fluorescent label in at least one spatial direction, so as to obtain sub-resolution spatial information regarding one or more fluorescently labeled objects in the region of interest, said sub-resolution spatial information comprising information about the spatial position of the one or more objects, and/or the size of the one or more objects; and/or the distances between the objects in at least one space direction.

According to an aspect, the processing unit may be further configured to perform a fitting of a model function $f(x,y)$ to the acquired acquired fluorescent emission distributions from the single fluorescent molecules in each of the two dimensional images of the time series:

$$f(x, y) = A\exp\left(-\frac{(x_0 - x)^2 + (y_0 - y)^2}{2\sigma^2}\right) + B_0 + B_1(x_0 - x) + B_2(y_0 - y),$$

wherein x and y are Cartesian coordinates in an object plane, perpendicular to the optical axis of the microscope;
$x_0$ and $y_0$ are the starting parameters for the position, which are determined as the center of the segmented signal;
A is the amplitude of the distribution, and
$B_0$, $B_1$, $B_2$ are parameters describing linear background.

According to a further aspect the processing unit may be further configured to process an additional wide field image data obtained by using wide field fluorescent microscopy with structured illumination light, so as to obtain additional spatial information comprising information about the spatial extension along a further spatial direction of at least one fluorescently labeled object in the sample and/or additional spatial information of the positions of the barycenters of the detected fluorescence emission distribution of the single fluorescent molecules in the at least one further direction. The at least one further direction may be along the optical axis of said microscope. The processing unit may be further configured to combine the localization information obtained by the localization microscopy with the additional spatial information obtained by the wide field fluorescence microscopy using structured illumination light.

In an aspect the processing unit may be configured to:
  generate a common theoretical three dimensional model function for all detected signals within the one or more objects, wherein said three dimensional model function is divided in plurality of two dimensional layers along the optical axis, and perform a lateral cross correlation of the acquired three dimensional image data and said three dimensional model function, wherein the maxima of the correlation function represent both one object identification and one three-dimensional localization.

A processing unit may be further configured to applying a threshold method to the obtained correlation maxima.

The processing unit may comprise an appropriately programmed general purpose processing chip, or a dedicated hardware. The processing unit may be connected to the storing means and configured to read data stored in the storing means.

The above methods and apparatuses (microscopes, respectively microscopic systems) according to any of the aspects of the present invention allow precise determination of object positions and have the potential to circumvent the optical resolution limit given be diffraction theory. In order to use localization to obtain structural information far below the diffraction limit, the "point like" components of the structure have to be detected independently, even if their distance is lower than the conventional optical resolution limit.

According to an aspect of the invention the conventional SPDM/SALM concept has been extended by exploiting intensity illumination in the range of 1 kW/cm$^2$ to 1 MW/cm$^2$ (a range which have been previously avoided in the fluorescence localization microscopy) and transitions between three fluorescent states. Such transition may be realized for example by the employment of novel spectral signatures offered by reversible photobleaching of fluorescent molecules, in particular fluorescent protein molecules. One advantage is that "conventional" fluorescent proteins, i.e. proteins without the chemical modifications described for PALM and FPALM application, may be successfully utilized for the purposes of sub-resolution fluorescence microscopy. Since biological specimens labeled with such fluorescent proteins are most common, the methods according to an aspect of the invention employing such fluorophores have a vast range of applications, including the potential for in-vivo measurements. Another advantage is that it is possible to achieve single molecule lateral (x,y) localization accuracy below 10 nm not only for special photoactivatable fluorescent proteins, but also for "conventional" ones.

Still other advantages are the short data acquisition and data processing times. In an example, the typical data acquisition rate is about 100 s in which an object area of up to 90 μm×90 μm could be recorded and considerably more than 100,00 molecules localized. The data processing aspect of molecule localization currently takes time in order of few minutes. By using fast modern dual-core processors, it is possible to carry out calculations on-line during image acquisition. Hence, high throughput fluorescence imaging at molecular optical resolution applying visible light in combination with widely used flurophores becomes feasible.

Another aspect of the invention, relates to a combination of this technique (i.e. SPDM/SALM lateral ((x,y)) localization microscopy) with Spatially Modulated Illumination (SMI) microscopy techniques for axial size dz and/or mean position $z_0$ determination. This novel technique allows fast three dimensional (3D) imaging of nanostructures, in particular biological nanostructures with an effective 3D optical resolution (x, y, z) of single molecules of approximately 20 nm in the lateral and 50 nm in the axial direction corresponding to about $\frac{1}{25}^{th}$ to $\frac{1}{10}^{th}$ of the exciting wavelength. For the application of the combined SPDM/SMI 3D imaging approach, some a-priori information about the labeled object may be required. This condition, however, can be fulfilled for most nanostructures, in particular for most biological nanostructures to be analyzed.

One example of an application of the combined extended SPDM/SMI technique is to elucidate the 3D cell structures of small cell protrusions by using membrane associated proteins. In one example the rod-like 3D structure of such a protrusion with a diameter around 50 nm was elucidated for the first time using a wide field fluoresce microscopy approach. Such almost ultrastructural 3D resolution is almost impossible to obtain by a conventional confocal laser scanning microscopy.

As the achievable effective three dimensional (3D) optical resolution may be increased to about 20 nm laterally and 50 nm axially (and higher), numerous applications in the structural elucidation of cellular nanostructures are feasible. Examples for such application are individual gene domains in the genetically active and inactive states; environmentally induced changes of chromatin nanostructures; size and nuclear distribution of replication factories and repair complexes; nuclear pore complex distribution; arrangement of polyribosomes; distribution of ion channels on the cell membrane, etc. Another important application is the possibility to count single molecules, for example on the cell membrane, or RNA transcripts. Although the SPDM procedure so far allows to register only a part of all labelled molecules, the numbers obtained are minimum absolute numbers. For example, an SPDM count of 100,000 proteins in a cell membrane (including both the upper and the lower side) of 20×20 y 2=800 μm$^2$ would result in a minimum mean absolute membrane density of 125 proteins/μm$^2$ or one protein in 90 nm×90 nm. Furthermore, it would allow to assess the homogeneity of molecule distribution at a resolution level in the macromolecular range. Numerous applications of such molecule counting and distribution analysis may be envisaged, from "fundamental molecular biophysics" to the efficiency of pharmaceutical compounds transport across the cell membrane.

In case sufficiently photostable fluorochromes with photo-convertible "dark" and "bright" spectral signatures are used, form the point of SPDM/SMI microscopy a further improvement of 3D effective resolution may be achieved. For example, if 5,000 to 10,000 photons could be registered from a single molecule, under else ideal conditions an improvement of the axial localization accuracy, up to an axial ($z_0$) localization accuracy around 1 nm is achievable. To also achieve an improvement in the lateral localization accuracy, up to 1 nm with such photon numbers, in addition to axially structured illumination, laterally structured illumination may be used. Such an improvement in x,y,z localization would allow an effective optical 3D resolution in the 2 nm range and hence be sufficient to make possible wide field light optical structural analyses even of the components of macromolecular complexes in the interior of the cells. Some possible applications may be: single gene domains; the replication factories responsible for the doubling of the cellular DNA; the repair complexes responsible for the repair of environmentally induced genome alterations; the chromatin remodelling/silencing complexes responsible for the expression related modification of genome nanostructure; the transcription factories allowing the "reading" of the genetic code; the splicing factories processing the transcribed RNA; the nuclear pore complexes controlling the traffic between cell nucleus and the rest of the cell; the ribosomes translating RNA into proteins; the proteasomes controlling the decomposition of proteins; the ion channel complexes controlling the transport of ions across the cell membrane; or the cell junction complexes responsible for formation of tissues.

Accordingly, it is anticipated that the extended SPDM/SALM method according to an aspect of the invention and in particular a combination of this method with SMI and other novel developments in laseroptical nanoscopy will eventually bridge the gap in resolution between ultrastructural methods (i.e. with nm resolution) and visible light far field microscopy (conventionally hundreds of nm resolution) in such a way, that the same cellular structures can be imaged at almost similar (down to molecular) resolution. Such a "correlative microscopy" may provide an essential contribution to a direct insight into the "machinery" of life on the individual cell level, from the change in folding of the chromatin fiber at the activation/silencing of a gene, to its transcription, to the processing of the mRNA produced, to the transport to the cytoplasm through the nuclear pores, to the translation into proteins, to the assembly and disassembly of macromolecular complexes, up to the signal transduction at the cell membrane and to cell-to-cell interactions. Beyond these exciting prospects for the molecular biophysics of the cell, it is anticipated that laseroptical nanoscopy methods will also provide an additional valuable tool for the analysis of the interaction of "biomolecular machines" (BMM's) and pharmaceutical drugs on the level of single cells/singe BMM's. The extended SPDM/SALM far field fluorescence microscopy approaches according to an aspect of the invention may be applied not only for measurements in the fields of bioscience and the physics of biological structures but also in the material science. For example, wherever a surface nanostructure has to be characterized and fluorescence labelling of surface molecules is feasible, a fast light optical analysis would become possible and this complement the high resolution but also more time consuming measurements by electron microscopy.

Details of the invention as well as further features, applications and advantages are discussed in the following embodiments or examples with reference to FIGS. 1 to 10. All disclosed or shown features taken alone or in arbitrary combinations with each other can be the subject of the invention, independent of their combinations in the patent claims of their back references as well as independent of their formulation or representation in the description or in the figures.

BRIEF DESCRIPTION OF THE DRAWINGS

FIG. 8 illustrates the principle of a three dimensional sub-resolution measurements of a given fluorescently marked object.

FIGS. 9a and 9b show the corresponding histograms of the distribution of photon numbers registered per molecule for two measured Cal-51 cells.

DETAILED DESCRIPTION OF THE PREFERRED EMBODIMENTS

Figure 1:
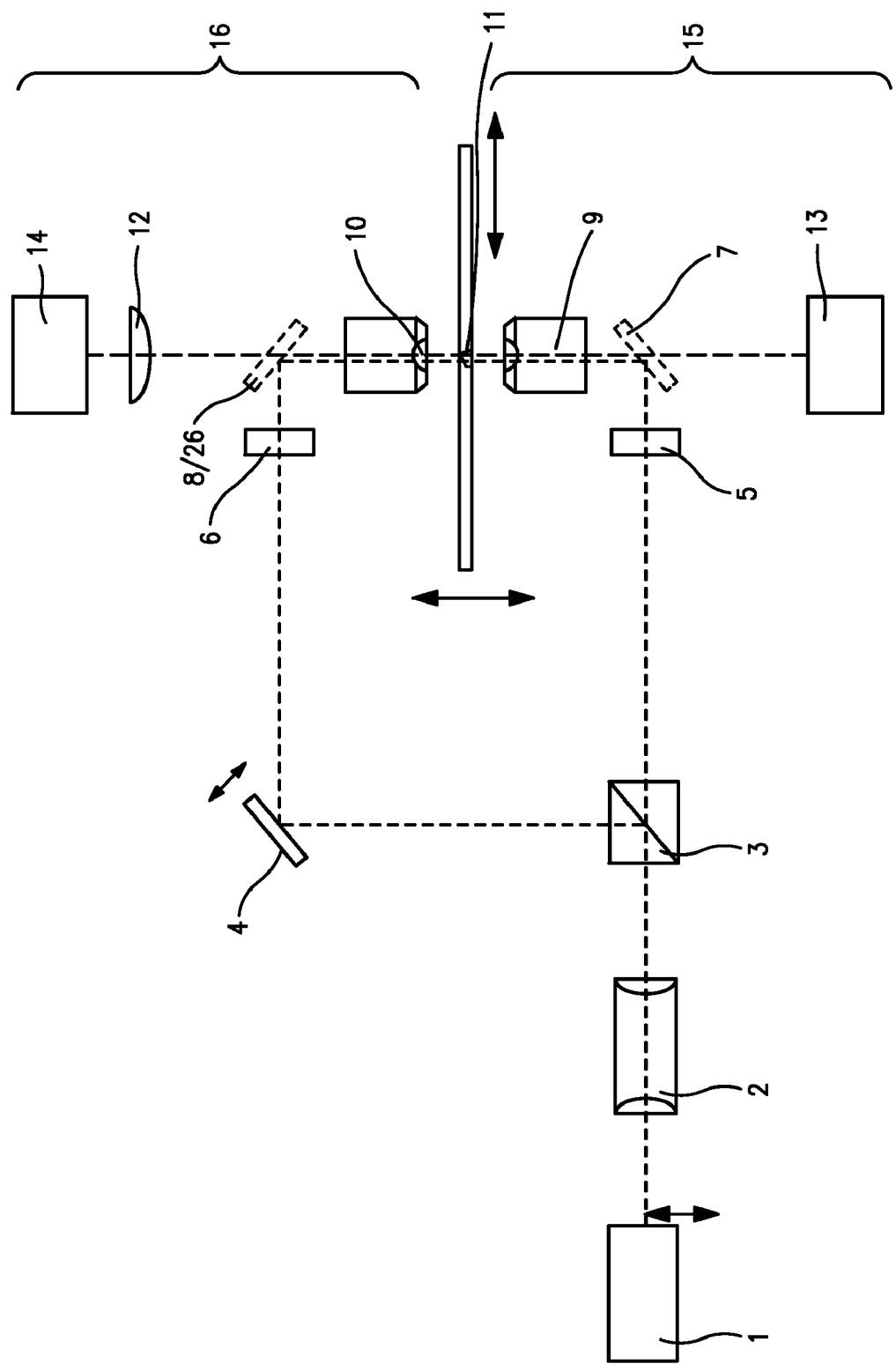
FIG. 1 shows one example of an apparatus with structured wide field illumination and a lens system, whereby two different detection optical paths are realized.

An apparatus (a microscope) according to an example of the invention is shown in FIG. 1. The apparatus comprises an optical light source 1, which is suitable for the emission of optical radiation with at least one wave length. The best value for money ratio is offered by lasers as optical sources. A movable lens system 2 is utilized to change over, respectively switch into, the intensity range used for localization microscopy after a wide field measurement using structured illumination light is completed. In addition the movable lens system may be utilized to adjust the intensity of the illumination light within the intensity interval of 1 kW/cm$^2$ to 1 MW/cm$^2$. For this purpose the optical radiation form the light source 1 is collimated to a thin ray with the use of the lens system 2.

In this example a periodic structured illumination is generated 17 between the first objective 9 and the additional second objective 10. The sample 11 can be freely moved through the structured illumination in the object space between the first objective (9) and the second additional objective 10. To achieve this, an interferometric set-up is realized with the help of the beam splitter 3. The mirror 4 is movable, thus enabling the change of the upper arm length of the interferometer with respect to the lower arm length. In this way it is possible to move or shift the structured illumination through the object space. The first focusing lens 5 and the second focusing lens 6 each focus in the rear focal plane of the respective objective and enable thus the generation of structured wide field illumination. The first dichroic beam splitter 7 and the second dichroic beam splitter 8 separate the excitation light of the source (dotted line) from the emission light (dashed line) coming from the sample 11.

The sample 11 is transparent for the light on both sides of the optical axis. In this way the photons emitted from the sample 11 in the direction of the first sensor 13 reach the first sensor 13. The same is also valid for the second sensor 14 and the photons emitted in the direction of the second sensor 14. If it is desirable to realize only the first detection optical path 15 which comprises, respectively is formed of the first objective 9, the second dichroic beam splitter 7 and the first sensor 13, then the second dichroic beam splitter 8 can be replaced by an additional mirror 26 and the cylindrical lens 12 and the second sensor 14 can be omitted.

The addition of the second detection optical path 16 alone improves the localization precision by about 40% at approximately isotropic radiation of the molecule due to the higher number of detected photons in comparison with the detection employing only one detection optical path 15. The employment of the cylindrical lens 12 further allows improving the axial localization precision with pure localization microscopy at the expense of the lateral localization precision.

The presented apparatus, respectively optical set-up is only one example of an optical set-up, which allows overcoming the limit of the localization precision with the pure localization microscopy by means of employing an additional far, respectively wide field analysis. The generated homogenously structured illumination is similarly only example of a structured illumination and can be replaced by other types of spatially structured illumination.

Figure 2:
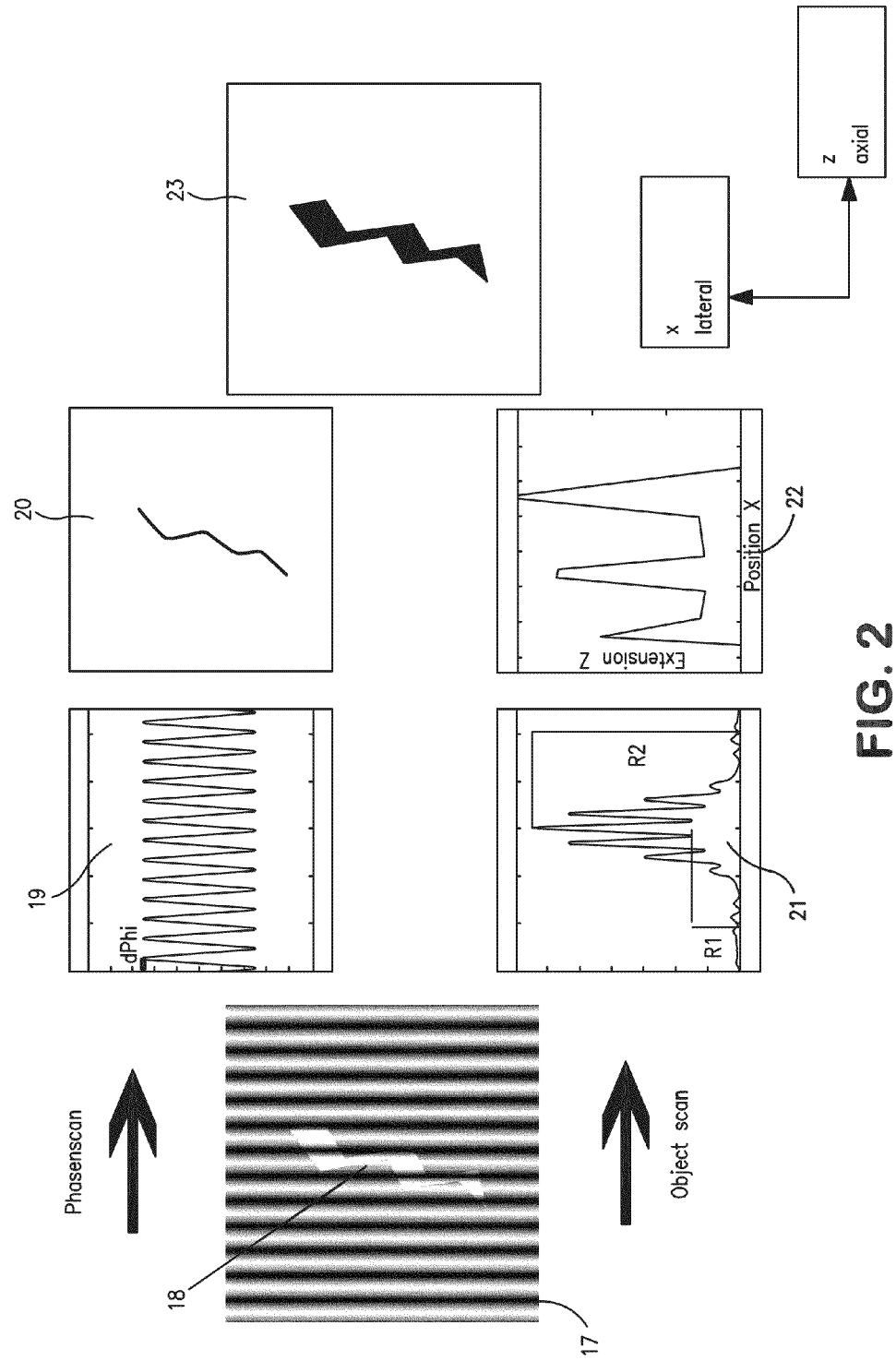
FIG. 2 shows an explanation of a method according to an aspect of the present invention.

A method for overcoming the limit for the localization precision is shown in detail in FIG. 2. For a more clear view one of the lateral dimensions (y) is disregarded, since it is completely equivalent to the other lateral dimension x.

The object 18 is initially subjected to the structured illumination 17. Two types of measurements may be thereby undertaken: The so-called phase scan at which the structured illumination 17 is shifted or moved and the object 18 is immobile, respectively not moved and the so-called object scan, during which the object 18 is moved relative to the static structured illumination 17 and relative to the static objective. A combination of both methods is also possible.

With any of the both scan methods the light emitted from the whole object 18 in the region of interest is detected by the sensor (for example a two-dimensional sensor) and the corresponding sensor image is stored in a suitable storage means. From the phase scan it is possible to extract the relative z-phase of each lateral point with a precision of a few nanometers by evaluating for each sensor element the resulting modulation 19. From this information it is possible to obtain the position of the barycenters of the fluorescence of the observed objects 18. From the object scan it is possible to extract with a precision of about a few nanometers the extension along the optical axis of each lateral point by evaluating for each sensor element the resulting modulation 21. The extension of the object 18 along the optical axis can be determined with a nanometer precision from the modulation contrasts (1−R1/R2, wherein R1 is the inner envelope of the modulation and R2 is the outer envelope of the modulation). In total full information about the position and extension of the object 18 along the optical axis 23 is obtained. For each laterally localized fluorescence molecule the axial position (relative phase converted to real distances) and the localization precision (extension of the object 18 can be determined with a nanometer precision. For the described far, respectively wide field measurement a single object scan or a single phase scan is sufficient. Optimal results can be achieved by a combination of the two scans as shown in FIG. 2, since the methods are differently suitable for obtaining different conclusions, respectively information. In FIG. 2 the reference sign 20 in is referring to the determination of the axial position of the emission's barycenter (object position) and the reference sign 22 is referring to the axial extension of the observed object along the z-axis.

Figure 3:
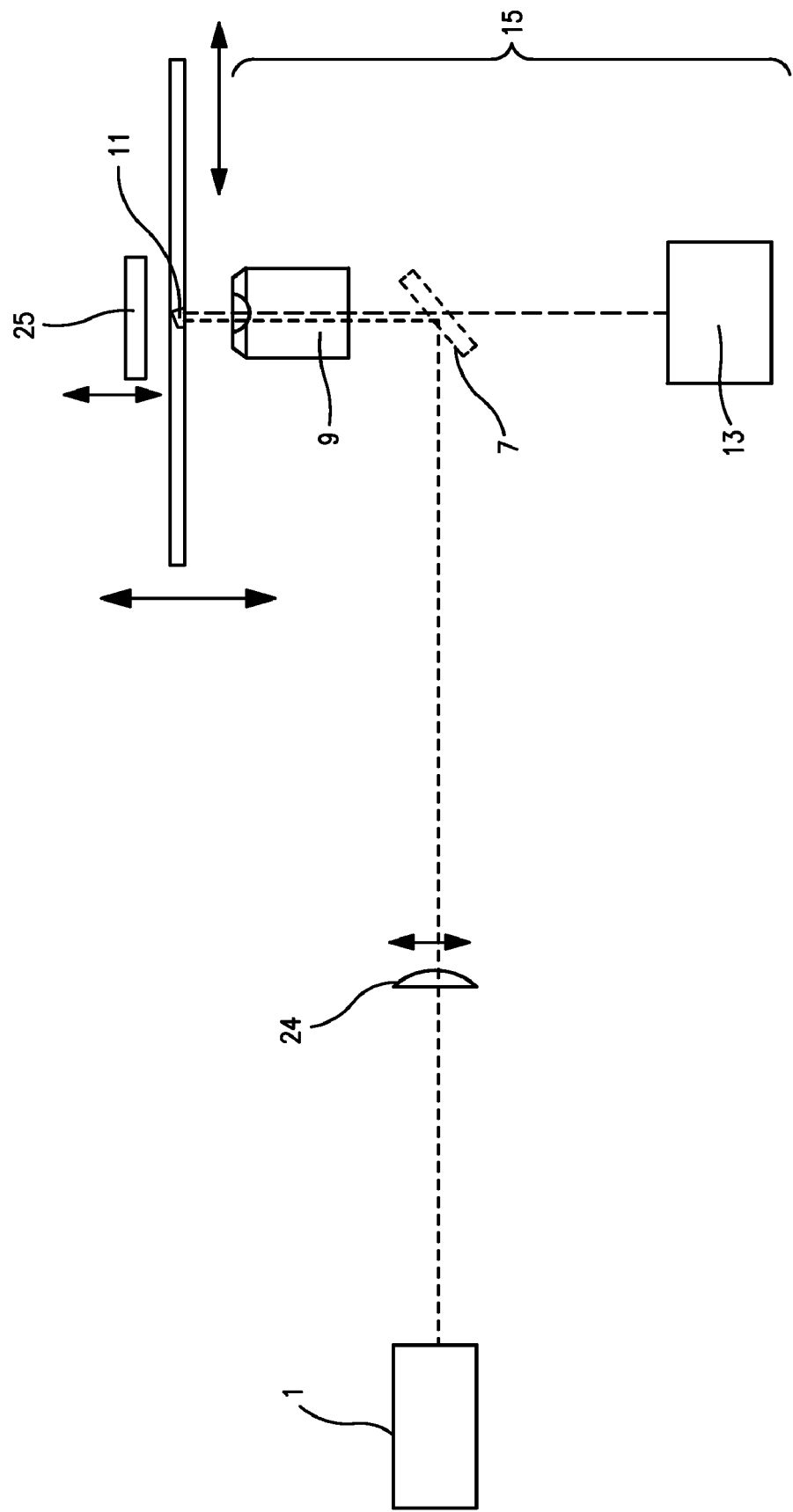
FIG. 3 shows a second example of an apparatus according to an aspect of the invention with a minimal number of necessary components.

A further example of an apparatus (microscope) according to an aspect of the invention is shown in FIG. 3. This apparatus uses a minimal number of optical and mechanical components. The illumination optical path consists only of a single source of optical radiation 1, a movable lens 24, a first dichroic beam splitter 7 and the first objective 9. The focal length of the lens 24 is determined such that a switch to and an adjustment of the intensity within the interval of 1 kW/cm² to 1 MW/cm² is possible. The excitation light from the source 1 (dotted) passes through the sample 11 and is back reflected by the movable mirror 25. Between the first objective 9 and the movable mirror 25 of standing wave field is built, which can be used for the far field examination in the above described way. The structured illumination can be shifted by means of a movement of the mirror 25. Equally an optical grating or a further optical element can be used to realize the structured illumination. With the above described method and the above described apparatus it is possible to realize a highly precise, fast and at the same time simple, economical and inexpensive localization of single dye molecules in the fluorescence microscopy.

Figure 4:
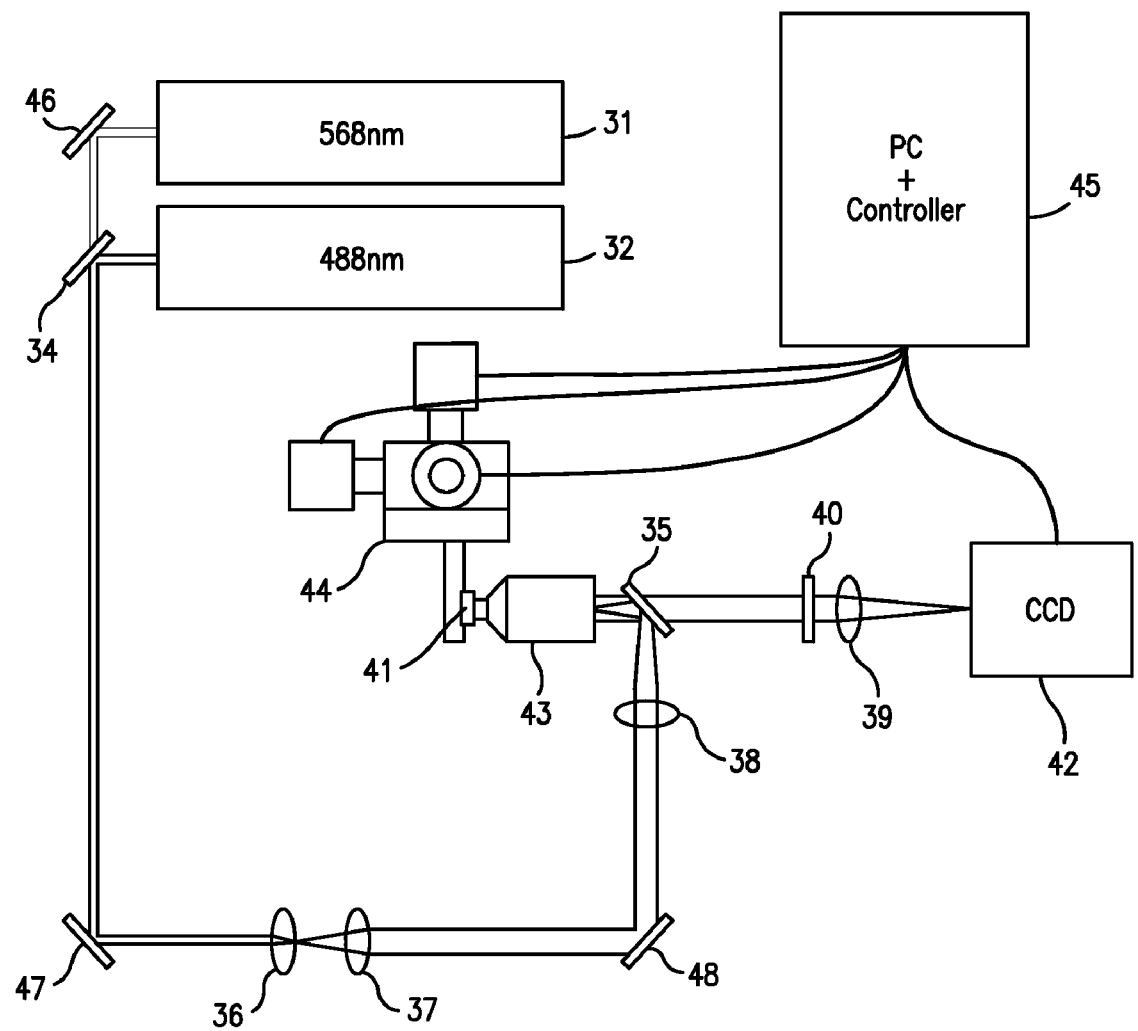
FIG. 4 is a schematic representation of a further example of a microscopic set-up employing localization microscopy (SPDM) according to an aspect of the invention.
Figure 5:
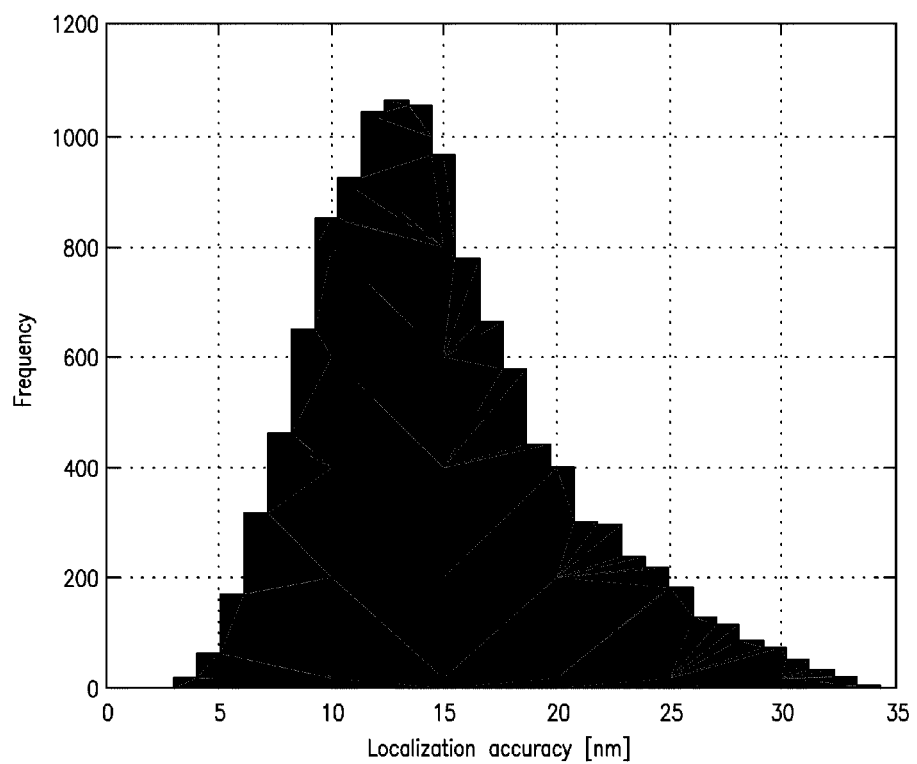
FIG. 5 illustrates an example of the frequency distribution of an estimated 2D—localization precision.
Figure 6:
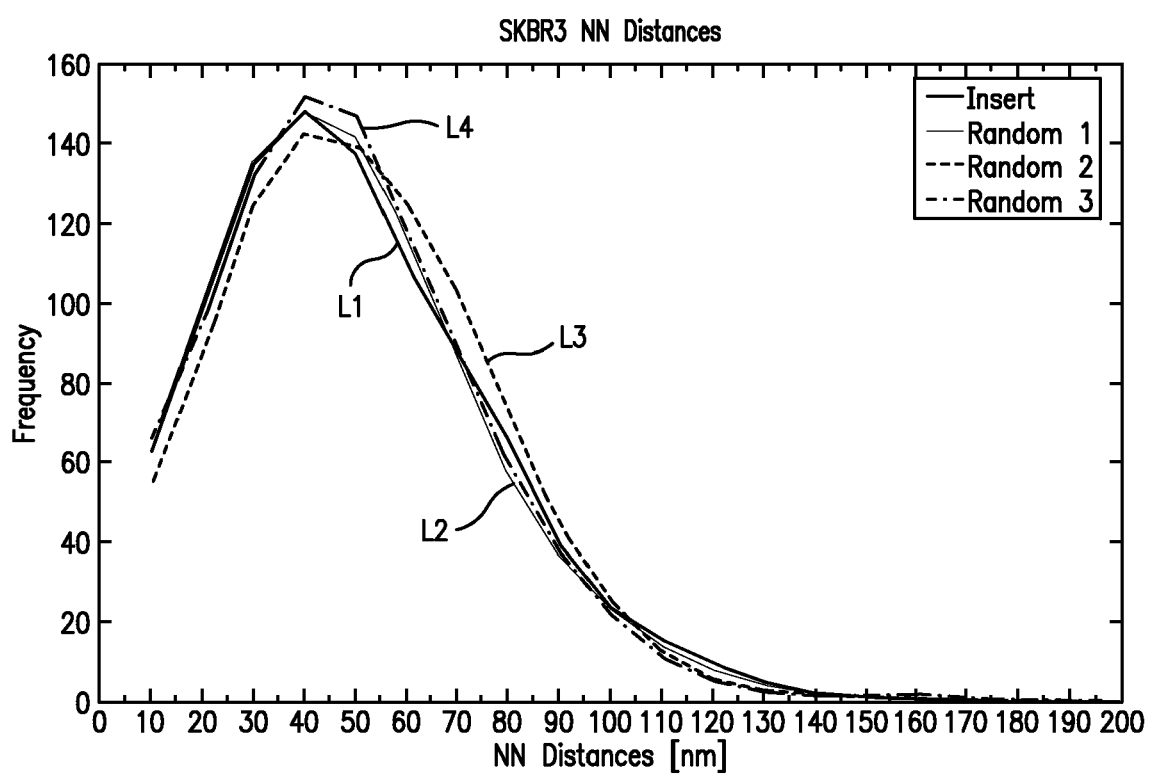
FIG. 6 shows a frequency distribution of the nearest neighbor distances for each localized fluorescent protein and the same analysis for three simulated random distributions of the same point density.

FIGS. 4 to 6 relate to still another example of an apparatus and a respective method for sub-resolution localization information in the nanometer resolution scale by employing an SPDM with conventional fluorochromes that show "reversible photobleaching" or "blinking". As already explained above, the "reversible photobleaching" has been shown as a general behavior in several fluorescent proteins, e.g. eGFP, eYFP or eCFP, or mRFP upon illumination with high intensity light. The effect has been described as pH-dependent, usually occurring on a time scale of 10-100 s, which can be modified under laser exposure. Similar "blinking" mechanisms exist for other, non protein based fluorescent dyes, e.g. Alexa 488. Any fluorochrome of this family of excitation activated, reversibly photobleaching fluorochromes will be called with an acronym "PHYMOD" fluorochromes (PHYsically MODifiable fluorochromes).

Subcellular structures were labeled with different PHY-MOD fluorochromes and images acquired in a fast time sequence under appropriate focusing conditions of the excitation. In this particular example, a localization precision down to 5 nm could be achieved, and the measured structures visualized by far field light nanoscopy with an effective optical resolution down to the molecular scale in the range of 10 nm.

In FIG. 4 the principal set-up of the SPDM microscope is shown schematically. Specimens, respectively samples 41 prepared on standard glass slides according to routine biological preparation conditions were used. The prepared sample 41 is placed on a piezo-electrical stage 44 controlled by a controller.

The samples 41 can be imaged for example in a standard far-field epifluorescence mode or in a single molecule SPDM nanoscopic mode. Samples 41 labeled by PHYMOD fluorochromes are illuminated by a first laser 31 (for example an Ar+-laser 32 at 488 nm) or a second laser 32 (for example a Kr+-laser at 568 nm), which are focused by an objective lens 33, for example an objective lens with 100×/NA1.4, oil (Leica). Using additional tubus optics, this focusing may be modified in such a way that many fluorescent molecules in the observation volume are exposed by moderate to high laser power (about 1 kW/cm² to 1 MW/cm²) within a broad region of interest ("sub-critical focusing"). Under these conditions, PHYMOD fluorochromes exhibit their characteristic reversible photobleaching or blinking which is used to identify and spatially assign the localization of individual molecules.

In a specific example, about 10,000 to 100,000 single molecules could be detected in a region of interest of presently up to 70 µm×70 µm. Using a sensitive image acquisition camera 42 (for example SensiCam qe, PCO) with a quadratic pixel size of 6.45 µm×6.45 µm as an image information acquiring sensor, time series of two dimensional (2D) images are acquired with a repetition rate of about 10-16 Hz. A typical time stack of 2,000 images is generally acquired within approximately 2.5 min. The two dimensional images acquired by the camera 42 are stored in a storage unit, respectively storage means of a processing unit 45. The processing unit 45 may furthermore comprise, respectively implement the controller, controlling the piezo-stage. In addition the processing unit 45 may be configured to process the obtained series of images to obtain spatial and/or distance information. The processing unit 45 may be for example a general purpose computer, such as a personal computer, a dedicated hardware, etc. The processing unit 45 may furthermore comprise a graphical user interface, for example an interactive graphical user interface, enabling the display of the detected images and of the results of the image processing.

In FIG. 4 reference signs 34 and 35 denote dichroic elements (dichroic mirrors), reference signs 36 to 39 denote lenses or lens systems, reference sign 40 denotes blocking filter, respectively dichroic element to block the illumination light; reference sign denotes objective lens and reference signs 46 to 48 denote mirrors.

For localization and distance measurements between individual molecules, several computer algorithms carried out by the processing unit 45 can be employed. In one example, the PHYMOD fluorochromes can be detected along the acquired image series by division of each two subsequent images, which allows the detection of local intensity changes corresponding to appearing and disappearing single molecule signals. In a given image frame, all signals of PHYMOD fluorochromes are registered simultaneously, and a model function is fitted to their barycenter of fluorescence (i.e. "gravity center of intensity") in the original image. This accurate position determination may be performed by a non linear fit based on the Levenberg Marquard algorithm using an analytically calculated point spread function or a Gaussian distribution, both taking into account a background signal approximation. The positions can determined along with estimates of the individual localization precision, that are consistent with the estimates taking into account the acquired photon number of each signal.

After registration of the positions of the individual molecules through the whole image time stack, all these positions are assigned to one "merged" 2D image. To indicate the localization accuracy they can be spread by a Gaussian intensity distribution with a standard deviation equal to the mean localization precision of the respective molecules. Distance measurements can be obtained from the barycenter distances between these reconstructed positions taking into account the localization precision for error estimates.

In order to indicate the potential of the SPDM nanoscopy according to an aspect of the invention in cellular systems, as an example SKBr3 mamma carcinoma cells were grown on cover slides according to standard conditions and the plasma membrane and its protrusions were visualized using Organelle Lights™ (Invitrogen) according to the manufacturers protocol with YFP subjected to PHYMOD conditions. 20 or 48 hours, respectively, after the transduction the cells were fixed with 4% formaldehyde in PBS and embedded with ProLong® Gold antifade reagent (Invitrogen). In this way only proteins restricted to the cell membrane were labeled.

The so prepared human SKBr3 cells were measured using the above optical set-up. The individual YFP molecules in this cell could be localized with a precision estimate of about 14 nm on average and down to a minimum of 5 nm.

FIG. 5 illustrates the frequency distribution (ordinate) plotted as a function of the estimated 2D—localization precision in nm (abscissa) of measured 12,115 fluorescent molecules, with a mean localization precision of 14.8 nm. More than 500 molecules in this image exhibit a localization precision of better than 8 nm. From these localization data, distances can be determined in the 10-30 nm range.

FIG. 6 shows the frequency distribution (ordinate) of the nearest neighbor distances in nm (abscissa) for each localized fluorescent protein (line L1) and the same analysis for three simulated random distributions of same point density (lines L1 to L4). In FIG. 6 a nearest neighbor distance determination for all molecules within a predetermined region of interest is compared with three random distributions (uniform spreading) of the same marker density. The result shows that the fluorescent proteins are randomly distributed in this area. Structure information like local density as well as periodicity or orientation traits can be obtained out of the shape of the calculated curves.

Thus, it was possible to localize individual molecules in cell membranes by the SPDM nanoscopy according to an aspect of the invention. The results indicate that using PHYMOD fluorochromes, it becomes possible to acquire images in which distances in the 10 nm range are resolved using only slightly modified standard epifluorescence microscopic setups and conventionally labeled specimens respectively conventional fluorescent labels. This makes the technique easy to handle, fast and economical. The acquisition of an image stack of several thousand images takes a few minutes only. In this way even applications in live cell imaging become possible. PHYMOD fluorochromes are not restricted to yellow fluorescent proteins only. We successfully applied SPDM nanoscopy also to cellular specimens labeled with the following fluorochromes: eGFP, CFP, Alexa 488, Alexa 568. Position and distance determination at the low nanoscale offer the possibility for a large number of structural investigations. This opens new perspectives for correlative microscopy (light microscopy versus ionizing imaging techniques). For the example shown here we have so far only applied 2D-SPDM nanoscopy. With the combination of SPDM nanoscopy and SMI (Spatially Modified Illumination) microscopy or other techniques of structured illumination, 3D—imaging with an effective optical resolution in the range of few tens of nanometer is in principle achievable. These developments in high resolution fluorescent nanoscopy will offer new insights in cellular structure and function.

Thus, an aspect of the present invention concerns a novel technique of far field localization nanoscopy combining Spectral Precision Distance Microscopy (SPDM) and widely used fluorochromes like the GFP derivatives CFP, eGFP, YFP and eYFP as well as the fluorescein derivatives, such as Alexa 488 and Alexa 568. SPDM allows the surpassing of classical resolution limits in fluorescence far field microscopy by precise object localization after optical isolation in time. Based on the principles of this technique, a nanoscopic set-up was realized for laser optical precision localization and image reconstruction with highly enhanced resolution in intact cells. This allows in particular for nanometer spatial assignment of individual fluorescent molecules with subpixel precision which was achieved by means of excitation intensity dependent reversible photobleaching of fluorescent proteins and fast time sequential imaging under appropriate focusing conditions. The advantage of the technique is that it can be easily applied to cellular nanostructure analysis. Using genetically encoded yellow fluorescent protein, membrane structures can be determined by visible light with a localization precision down to 5 nm; hence distances in the range of 10-30 nm were nanoscopically resolved between individual fluorescent molecules allowing to apply different quantitative structure analysis tools.

FIGS. 7 to 10 relate to still another example of an apparatus (microscope) and a method employing SPDM/SALM in combination with Spatially Modulated Illumination (SMI) along the optical axis to carry out three dimensional measurements, in particular a three-dimensional (3D) single molecule localization and a corresponding 3D effective resolution.

The employment of the SMI Microscopy allows the determination of the axial extension (i.e. "size") of a fluorescently labeled nanostructure (at a given x, y position) down to a few tens of nm. For example, if the axial (z) extension dz of such a nanostructure has been determined to be 30 nm, this means that most of the molecules within this nanostructure have an axial distance from each other not exceeding 30 nm. Consequently, the smallest resolvable axial distance (or z-resolution) would also be around 30 nm; if a significant number of molecules would have a larger z-distance from each other, this would lead to a broader (z) extension than measured. In addition, the mean axial localization $z_0$ of these molecules is given by the maximum of the axial SMI intensity distribution.

From this general idea, the following approach was envisaged according to an aspect of the present invention. Firstly, the position interval dz of the molecules along the optical axis (z) is determined for every single (x, y) pixel. The smaller the axial extensions dz of the labeled nanostructures are the more precisely their markers, respectively labels (fluorescent molecules) can be localized along the optical axis, and hence the better the axial effective optical resolution will be (i.e. the smallest axial distance between two labeled molecules which can be detected). For example, if the lateral (x, y) localization accuracy is assumed to be 15 nm, and if the minimum measurable axial (z) extension dz is assumed to be 30 nm, then a lateral distance between molecules equal or larger then about 35 nm should be detectable, this should be detectable due the resulting broadening of the axial extension. From this, for this example, an overall 3D resolution around 40 nm may be estimated.

Optical Set-Up

Figure 7:
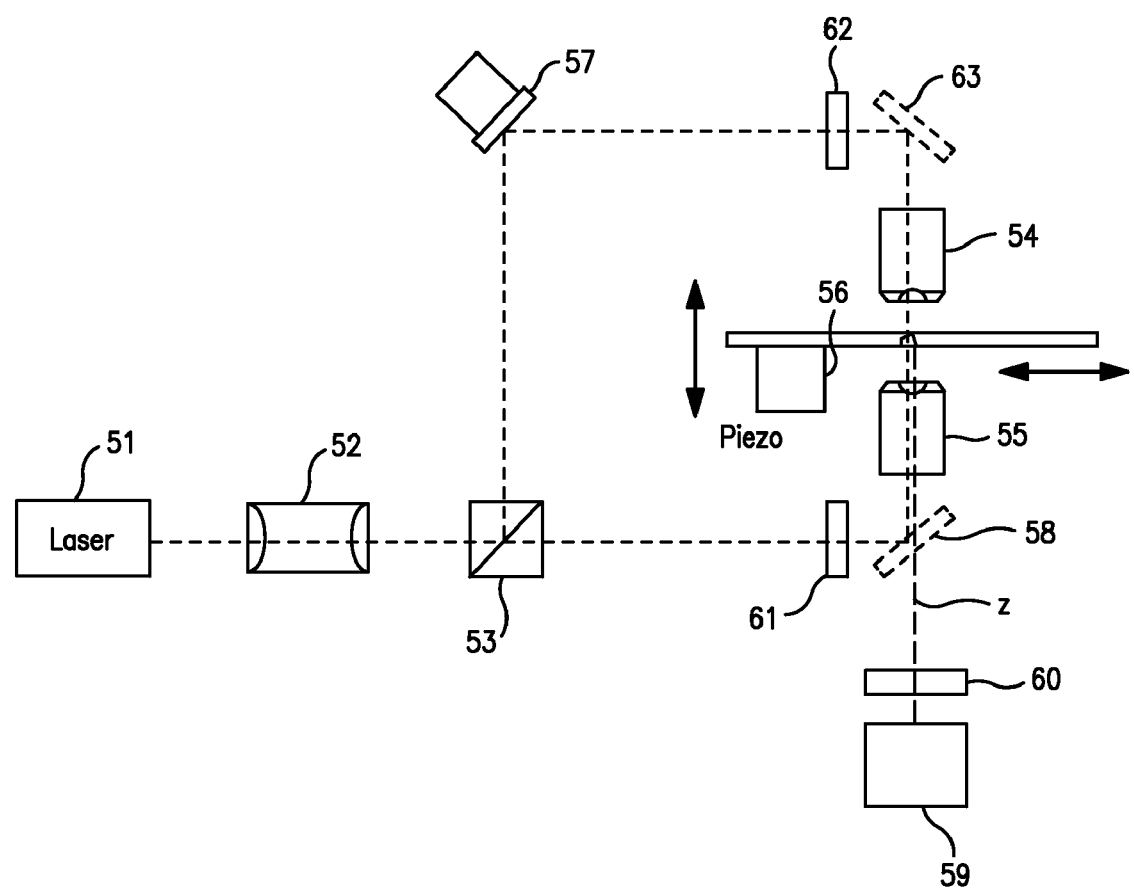
FIG. 7 is a schematic representation of still another example of a combined SPDM/SMI microscopic set-up according to an aspect of the invention.

FIG. 7 is a schematic overview of a combined SPDM/SMI optical set-up used to carry out sub-resolution measurements. One major improvement compared to a far field fluorescence microscope is the structured illumination pattern in the form of a standing wave field along the optical axis created between the two objective lenses. This standing wave field permits to obtain accurate size and position information along the optical axis z. A second detection path using the second objective and a further sensor can easily be established, allowing either the detected photon number to be doubled, or biplanar detection to be implemented, whilst retaining the same in-plane strength.

In this example a SMI microscopic set can be used to carry out SPDM observations with molecules subjected to reversible photobleaching. For illumination and excitation, up to three laser sources 51 are available for $\lambda_{exc}$=488 nm, 568 nm and 647 nm. The light sources 51 can be independently switched on and off with shutters before being combined with dichroic mirrors. The three laser lines are directed into the collimator 52, comprising two achromates with 10 mm and 100 mm focal lengths, respectively, to expand the beam to a diameter of approximately 20 mm. The expanded laser beam is then split by a 50:50 beam splitter 53, yielding two coherent counter-propagating and collimated laser beams, which are focused into the back focal plane of two opposing oil immersion objective lenses 54 and 55 (for example oil immersion lenses 100×, NA=1.4). This results in two counter-propagating collimated beams. Interference between these two beams produces a standing wave field in the space between the two objective lenses 54 and 55, and hence a $\cos^2$-shape distribution of the intensity along the optical axis z.

Samples may be prepared using ordinary object slides and/or coverslips and are then placed between the two objective lenses and moved along the optical axis with a piezo-electrical stage 56, allowing 3D image stacks of the specimens, respectively samples to be recorded. An additional piezo-electrical stage controlling the position of a mounted mirror 57 (Piezo Mirror) allows the relative phase in the two interferometer arms to be varied. The emission light from the fluorescently labeled target regions collected the detection objective lens 55 is then separated from the excitation light by a dichroic mirror 58 and focused by a tube lens (not shown) onto a highly sensitive 12-bit black-and-white CCD camera 59 for imaging. In front of the CCD chip, a blocking filter wheel 60 blocks any remaining excitation light and, depending on filter selection, out of band fluorescence. Moreover a while light emitting diode can be used in transmission mode to locate the focal plane in order to reduce bleaching of the dyes. In FIG. 7 the reference signs 61 and 62 denote respectively a first (61) and a second focusing (62) lenses and the reference sign 63 denotes a mirror.

Data Acquisition

The combination of SPDM/SMI methods for high resolution 3D imaging uses two different acquisition processes, a SPDM localization image acquisition process and a SMI image acquisition process.

First, SMI images are taken at low illumination intensities with negligible bleaching. A typical intensity is about 100 W/cm$^2$ and camera integration time of 100 ms per frame. For this, the object and the structured illumination are moved relative to each other in discrete steps ($\Delta z$) of typically 20 to 40 nm. In case the object is stationary and the structured illumination is moved by for example adjusting the Piezo Mirror 57 of the optical set-u shown in FIG. 7, this is called a phase scan. Otherwise if the object itself is moved in the standing wave field by for example adjusting the piezo stage 56 in the optical set-up shown in FIG. 7, the process is called an object scan. Each of the phase and the object scan yields the desired axial information. After each $\Delta z$ step a wide field image is recorded by the CCD camera, and all the images (in a specific case about 200) are saved on a suitable storage medium within a first datastack, called a z-stack.

After the SMI mode registration is completed, data acquisition for the 2D SPDM localization is performed at high laser intensities of about 1 kW/cm$^2$ to about 1 MW/cm$^2$. In one implementation only one laserline ($\lambda_{exc}$=488 nm) is used for all measurements. No further object movement is necessary during the 2D SPDM acquisition process. Applying frame rates of 10 fps to 18 fps (fps—frame per second) the individual wide field images (about 1000 to 3000 per object) are saved in sequence within a second datastack, called a time stack.

The region of interest may be the same for the two acquisition processes. The region of interest may be set for example to 100 µm$^2$ to 5000 µm$^2$, depending on the structure of interest.

Data Evaluation

2-D Localization

After the data acquisition, the first evaluation step may be the 2D SPDM localization. Since the source of the acquired signal is a "point-like" molecule (i.e. diameter$<<\lambda_{exc}$), for the evaluation the knowledge of how "point-like" objects are imaged by the microscope system may be applied. Based on this knowledge, a model function may be fitted to the acquired signals taking into account effects of data sampling (size and distance of the pixels of the CCD camera) and the corresponding noise nature.

To use the noise considerations of the fitting algorithm in an appropriate way, a conversion from camera counts to photons may be performed, using in particular information about the quantum efficiency in the specific light mode (for example low light mode) of the CCD camera, which is usually provided with the manual of the CCD camera and an information about the Analog/Digital (A/D) conversion factor in the specific gain mode. In one example the used CCD camera is a 12-bit black-and-white camera (SensiCam QE, PCO Imaging, Kelheim, Germany), for which in low light mode the quantum efficiency for YFP emission radiation between 490 and 560 nm is 64±1% or 0.64 e$^-$/photon. Taking in mind that the Analog/Digital (A/D) conversion factor in this high gain mode is 2e$^-$/count, the count number is multiplied by 2/0.64 photons/count=3.13 photons/count.

The fitting process may be carried out using for example two different implementation of the Levenburg-Marquardt algorithm with a Gaussian distribution $f(x,y)$ of photons and model function for the signal in the object plane:

$$f(x, y) = A\exp\left(-\frac{(x_0 - x)^2 + (y_0 - y)^2}{2\sigma^2}\right) + B_0 + B_1(x_0 - x) + B_2(y_0 - y).$$

In the above formula $x_0$ and $y_0$ are the starting parameters for the position, which ware determined as the center of the segmented signal. A is the amplitude of the distribution, and $B_0$, $B_1$, $B_2$ are parameters describing linear background.

This first fitting algorithm solves the weighted least squares problem considering the known noise model of the signal acquisition (Gaussian read-out noise of the detector combined with Poissonian photon and conversion noise). The second fitting algorithm is least squares algorithm. Both algorithms are computer implemented and may be implemented in various programming languages or software packages executed on a general purpose or a specialized computer or computing hardware or on a network of computers.

The origin of the signal, and hence, the position of the source molecule (i.e. the fluorescent molecule, which is the source of a particular signal) can be determined laterally (i.e. in the object plane x, y) with an accuracy (standard deviation) $\sigma_{lat}$ of less than 5 nm (localization accuracy). Under the conditions used in the second embodiment, the localization errors resulting from the unknown orientation of the molecules may be neglected. Since the limit of the localization accuracy can be estimated by the relation $\sigma_{lat} \approx \lambda_{emission}/[NA*n_y^{1/2}]$, given the emission wavelength $\lambda_{emission}$, the numerical aperture of the optics NA and the number of detected photons $n_y$, the main limitation of the localization precision is the number of the collected photons.

3D Localization

The principle of 3D localization is summarized in FIG. 8. An exemplary nanostructure of interest (i.e. object of interest) with lateral (x,y) and axial (z) distribution is shown in FIG. 8a. All molecules of the nanostructure at a given x,y position are assumed to have an axial extension less than approximately 130 nm (for example dz 60 nm). The object of interest (FIG. 8a) is placed within a standing wave field along the optical axis and excited by it as shown in FIG. 8b. Either the standing wave field (phase scan) or the object (object scan) is moved in equal steps (for example $\Delta z=20$ nm-40 nm). FIG. 8c shows the detected intensity distribution along the z-axis for a phase scan, FIG. 8d shows the detected intensity distribution along the z-axis for an object scan.

At each step the fluorescence emission is detected and saved separated in one frame. All the frames then are saved into a 3D data stack (z-stack) displaying the axial mean position $z_0(e)$ as shown in FIG. 8e, which is obtained from the maximum of the intensity distribution shown in FIG. 8d. Evaluating the scan data (phasescan data shown in FIG. 8c or object scan data shown in FIG. 8d), the spatial extension dz of the object, which is determined from the contrast in modulation $$r = \frac{max - min}{max},$$

where max is the maximal intensity and min is the minimum intensity along the time axis (corresponding to the z-coordinate) can be obtained with a precision of a few nanometers. FIG. 8g shows the mergend axial (z) data for all pixels of the lateral (x, y) region of interest.

The interpolated axial information (FIG. 8g) can then be combined with the single molecule positions of the 2D SPDM localization, resulting in a 3D image with an effective 3D optical resolution at the nanoscale, which is shown in FIG. 8h. In one example the resulting 3D SPDM image, has an effective 3D optical resolution of about 30 nm lateral effective optical resolution (obtained from the x,y localization microscopy) and 40 nm axial effective optical resolution (obtained form the z-extension measurements). If only one fluorophor with sufficient photostability is excited along the z-axis its z-position may be monitored by SMI with an accuracy even in the 1-2 nm range.

Below are some examples of the application of the above method and optical set-up to sub-resolution measurements of biological structures.

Sample Preparation

As a first application example for using the above described high resolution 3D SPDM/SMI for imaging of biological nanostructures, the plasma membrane of the human breast cancer cell line Cal-51 labeled with Yellow Fluorescent Protein (YFP) was analyzed.

Cal-51 breast cancer cells of human origin were routinely cultivated win DMEM medium supplemented with 10% FCS, 1% L-glutamine and 1% penicillin/streptomycin at 37° C. and 5% CO2 in a humidified incubator. The cells were then seeded onto 20×20 nm coverslips and grown over night at 37° C. and 5% CO2 in a humidified incubator. Labeling of the plasma membrane was performed by Organelle lights (Invitrogen Corporation, Carlsbad, USA) according to manufacturer's protocol. The kit is based on genetically encoded fluorescent proteins (YFP) fused to signal peptides that direct the fluorescent markers (label) to specific cellular compartments, in this case the plasma membrane. Cellular delivery is achieved by BacMam technology, based on the baculovirus. The cells were then incubated for 24 h at 37° C. and 5% CO2 in a humidified incubator and subsequently fixed in 4% formaldehyde in PBS to stabilize the cell structure. The transduction efficiency was about 60%.

The cells were mounted with ProLOngGold antifade reagent (Invitrogen). One drop of antifade reagent was placed onto an object slide and the cover slip, with the cell side down, was carefully lowered onto it. The slides were sealed with nail polish and stored at 4° C. in the dart until usage.

Example 1

Two-Dimensional SPDM Reconstruction

As a first application example, the SPDM microscopical method according described above was used for the two dimensional (2D) reconstruction of the distribution of membrane proteins. For this example cells of human breast cancer Cal-51 were labeled with yellow fluorescent proteins (YFP). During the SPDM imaging process, the YFP molecules were subjected to an appropriate physical modification based on reversible photobleaching as described above. For smoother appearance and to indicate the localization precision, the pixels (10 nm pixel size) corresponding to the positions and number of the localized fluorescent proteins were blurred via a Gaussian kernel with 15 nm standard deviation. In this example, the (x,y) width of the finest structures resolved (cellular protrusions) in the SPDM images amounted to about 50 nm-60 nm. The number of collected photons per molecule distribution (FIG. 9) allows to estimate the limiting localization accuracy due to photon statistics to be in the range of 6 nm; this is compatible with the experimental localization accuracy of about 15 nm obtained by the fitting procedure (FIG. 10).

FIGS. 9a, b show histograms of the distribution of photon numbers registered per molecule for two CAL-51 cells observed. The mean photon numbers estimated are 1,361 for the distribution shown in FIG. 9a and 1,080 for the distribution shown in FIG. 9b. The total number of localized protein molecules is 12,691 for the example shown in FIG. 5a and 6,871 for the example shown in FIG. 5b.

Figure 10:
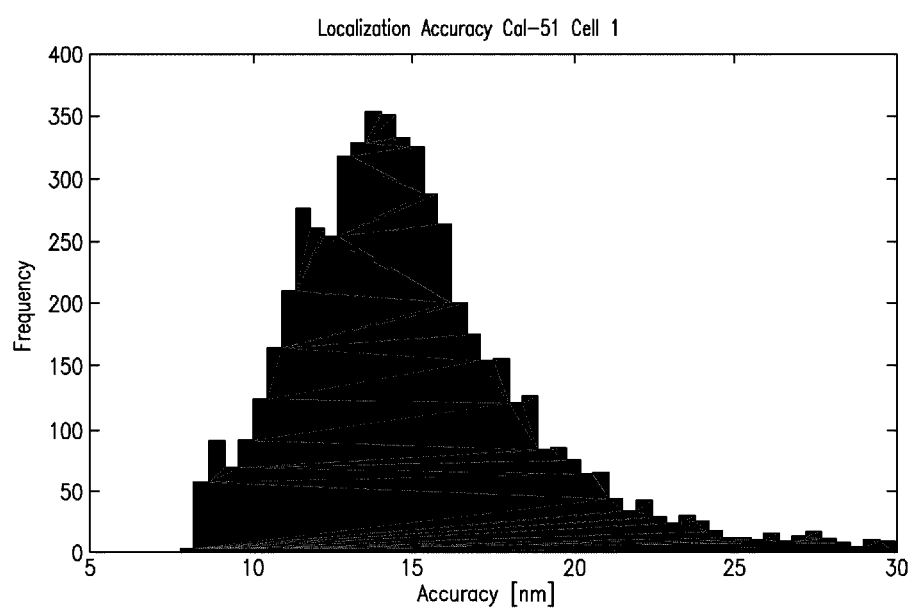
FIG. 10 shows a histogram of localization accuracy (pair-wise mean value of x and y localization precision) for a measured Cal-51 cell.

FIG. 10 shows histogram of the localization accuracy (pairwise mean value of x and y localization precision) for one of the Cal-51 cells, which photon distribution is shown n FIG. 9a. The overall mean value of the localization precision is 14.9 nm with a standard deviation of 3.9 nm. The total number of fluorescent molecules is 12,691.

In both cases, the total data acquisition time was about two and a half minutes while 2000 wide field images were recorded at an average frame rate of about 13 frames per second. The mean photon numbers per molecule registered was about 1,300 for the cell shown in FIG. 9a and 1,100 for the cell shown in FIG. 9b. The fitting procedure takes about 3 to 10 minutes on a single core conventional PC without implementation of acceleration methods. The relevant values (photon number, localization accuracy and the number of localized molecules) were very similar throughout the whole series of more than 100 SPDM images, which were acquired from two specimens within a few days.

Example 2

Three Dimensional SPDM/SMI Reconstruction

The second example relates to a three-dimensional SPDM/SMI reconstruction of a Cal-51 cell (plasma membrane labeled with physiochemically modified YFP) by first imaging in wide field mode with spatially modified illumination ($cos^2$ intensity distribution along the optical axis). The standing wave field was moved with a step size $\Delta z=25$ nm for 5 µs (phase scan). The emission of the cellular plasma membrane protrusions was recorded for every $\Delta z$ step. Compared to the experimentally effective wavelength ($\lambda_{exc}/n \approx 330$ nm) and the accuracy of the z-positioning of the piezo actuator 84 nm standard deviation), this process corresponds to a large oversampling. However, since the total acquisition time was about 20 seconds, there was no need to use larger step sizes or fewer steps.

By performing a single dimension Fourier transformation along the time axis, and knowing the wavelength of the light pattern (330 nm), the phase was determined for every lateral (x, y) pixel of the stack. To obtain the position of the emission center for every pixel, the phase was shifted by $\pi/2$ and multiplied with the wavelength of the modulated illumination.

To determine the extension dz of the object along the optical axis, the modified contrast $R_{mod}=I_{max}/I_{min}$ was calculated from the information stored in the SMI mode images. Using the Fourier domain, the amplitude and the constant contingent of the modulation were directly determined after adjusting the zero level by subtracting the background, In the next step, the contrast image was correlated with the corresponding structure sizes.

Structure elements with small axial extension (Ø) correspond to an object scan intensity distribution with a low modified modulation contrast $R_{mod}$. In the structure is supposed to be tube-like and homogeneously labeled, the following relations may be estimated for a $cos^2$ shaped standing wave field produces with 488 nm excitation light:
$R_{mod}=10\% \Rightarrow \text{Ø} \approx 50$ nm,
$R_{mod}=40\% \Rightarrow \text{Ø} \approx 140$ nm,
$R_{mod}=70\% \Rightarrow \text{Ø} \approx 190$ nm.

The next step after the analysis of axial positions $z_0$ and extensions dz was two-dimensional (2D) SPDM localization of the singe molecules in the same object.

Then the obtained 2D localization image (x,y) data was combined with the SMI ($z_0$) position and size (axial extension dz) information to obtain a three dimensional positional information. In the specific case, very small cell protrusions could be observed, both in x,y width (minimum width about 55 nm) and in the z-direction (minimum $\Delta z$ about 50 nm). Hence, it was determined that the structure of this protrusion is compatible with that of a rod of about 3 µm in length and ca. 50 nm in diameter.

In the above example only one type of molecules (cell membrane bound proteins) was imaged by SPDM/SMI. For this, only one laser line was used for excitation and the emission was limited to a small wavelength band. The above method can be, however, extended to appropriate multicolor SPDM/SMI with several excitation wavelengths and appropriately discriminated emission spectra. In this case, the chromatic aberrations may have to be considered. Using high quality objective lenses, these can still be as large as 50 nm in lateral (x,y) and in axial (z) direction. Accordingly, special care has to be taken in multicolor SPDM/SALM imaging to correct for these aberrations by appropriate in situ calibration procedures.

The present invention relates furthermore to one or more of the following aspects:

According to an aspect there are provided a method and apparatus for localization of single dye molecules in the fluorescence microscopy, with the help of which the fluorescence dye molecules, which are used for the labeling of the sample, respectively object to be observed, respectively analyzed, are transferred statistically and individually from a non fluorescent state to a fluorescent state and by means of emission of fluorescent light to a long lasting inactive state.

Their fluorescence is collected on an information acquiring sensor and a subsequent localization of the individual fluorescent molecules in the image space is carried out. The object information for at least one fluorescently marked, respectively labeled object to be observed is obtained on the basis of the object's observation with the help of at least one wide, respectively far field method and under employment of at least one type of structured illumination, from which the spatial extension of the observed fluorescently labeled object in at least one space direction and the barycenter position of the dye in this direction are determined. In addition one suitable window for the intensity of the optical radiation, lying within the in the fluorescent microscopy avoided range of 1 kW/cm² to 1 MW/cm², is determined, in which the fluorescent single dye molecules in their signal are localized temporarily separated by means of a localization microscopy. The obtained object information and the results of the localization microscopy are combined, thus enabling to overcome the limitation of the localization precision, which appears with a purely photon dependent localization of the observed dye molecules. Accordingly a maximal under these circumstances localization precision of the individual dye molecules is achieved.

According to the above aspect, the localization microscopy is combined with far-field microscopical observations with structured illumination. Thus, it is possible to overcome the limit for the localization precision or accuracy along the optical axis at otherwise identical conditions of the localization-microscopical observation. Depending on the art, respectively type of the structural illumination it is possible to determine with a precision of up to few nanometers the size of the fluorescently marked object structures, which exhibit smaller extension, respectively size than the distance between the maxima of the intensity in the structured illumination. The same applies also to the position of the center, respectively barycenter of the marking, respectively labeling. Since with a localization microscopy one is primarily interested in very small structures, it is known immediately after one lateral detection and localization of the signal in which "depth" (barycenter of the labeling) the molecule must be lying and with which precision its position was determined (extension of the object). In this way it is possible to carry out three-dimensional single molecular localizations with an absolute precision (no standard deviation) of under 40 nm in axial and under 10 nm (about 4 nm standard deviation) in lateral direction even at quite poor photon yields.

According to an aspect a far field observation, respectively measurement of the object can be carried out in advance. This allows to make some important conclusions or assertions about the object itself before the object is reconstructed with the localization microscopy. Thus it is possible for example to estimate in advance how well the labeling has been carried out. Crude or relatively great changes in the structure such as for example current or flow processes can be measured in vivo.

The detection, respectively collection of data according to an aspect can be carried out within fewer than five minutes, which represents a difference of up to two orders in comparison to alternative methods requiring up to several hours. This is particularly advantageous for in-vivo observations in living systems. Thus, it is possible to avoid demanding and complicated technical solutions, which may counter or alleviate drift problems or provide for maintenance of life of the observed samples. In contrast, with the proposed method it is possible to carry out a meaningful in vivo observation also on the smallest structures.

Instead of fluorescent molecules it is also possible to employ phosphorescent molecules in order to improve the in vivo applicability of the proposed new method. These molecules enable localization over a longer period of time.

According to a further aspect a spatial calibration of the structured illumination may be carried out with the help of at least one fluorescent reference point. By using a calibration method and the employment of at least one fluorescent reference point, with the aid of which the location, respectively position and the intensity of the standing-wave field can be directly measured and oriented, it is possible to optimize the utilization of the structured illumination. Therewith it is possible to describe the structured illumination with maximal precision. As a reference point, a thin, weakly fluorescenting layer on the coverglass of the coverslip, respectively sample preparation, such as for example layer of photo-lacquer, respectively photoresist, may be employed.

In a further aspect at least one fluorescence dye is used for the labeling, and during the far, and in particular wide field observation at least one, sufficient for the successful application of this method part of the fluorescence dye molecules is in an active state and is used for the corresponding observation. One further part of the fluorescence dye molecules remains in an inactive state and is activated only by means of the change or switch of the intensity of the optical radiation to one lying within the window of about 1 kW/cm$^2$ to 1 MW/cm$^2$. The imagining of the observed fluorescently labeled object in the localization microscopy is carried out on the basis of the second part of the fluorescent dye molecules.

Accordingly, it is possible to use for the far, respectively wide field observations initially inactive fluorescent molecules, if a sufficient portion of these molecules is activated for the purpose of the far, respectively wide field observation. The partial activating of the molecules for the purpose of the far, respectively wide field observation can be carried out for example with a second illumination wavelength. Different activating methods, such as for example thermal activation, can be also employed. The second portion of the dye molecules is employed for the subsequent localization in the localization microscopy. It is also possible to label the objects with a multiple labels comprising more than one types of fluorescent dyes, respectively dye molecules, so that one type of dye can be used for the far, respectively wide field observation and the other for the subsequent single molecule localization in the localization microscopy.

The used optical radiation may be monochromatic. Thus, it is possible to use one single wave length for the whole observation, respectively analysis process. The localization microscopy is carried out thereby within the intensity range of about 1 kW/cm$^2$ to 1 MW/cm$^2$. This brings economical and technical advantages over conventional systems, which employ solely localization microscopy and which employ at least two wave lengths for the activating, excitation and deactivating of the dye molecules. The number of parameters which must be varied can be thus reduced at least in half. Naturally the employment of more than one wavelength is also in accordance with the invention. This can be for example advantageous if the localization of multiple molecule types is aimed at.

According to another aspect an optimal intensity from within the range of about 1 kW/cm$^2$ to 1 MW/cm$^2$ is determined for every individual employed type of fluorescent dye, respectively fluorescent dye molecules. Thus, the achievement of maximal localization precision and number of localized dye molecules is assured during the imagining of the observed fluorescently labeled object in the localization microscopy.

In particular, it is possible to optimize the localization precision and the number of the localized molecules and thus the reconstruction of the localizing method by molecule-specific determining an optimal illumination within the intensity range of about 1 kW/cm$^2$ to 1 MW/cm$^2$. Since the localization precision and the number of the localized molecules often cannot be simultaneously maximized it may be necessary to make a compromise.

As already described above, the partially cyclical process course in the localization microscopy can be described as follows: a portion of the dye molecules, which are used for the labeling, is activated, wherein the density of the activated molecules must be lower than one molecule per diffraction limited detection volume. This volume can be well described with the help of the effective point-spread-function in that for example all points with intensity higher than for example the half of the maximum intensity of the point-spread-function are counted as belonging to the volume. After the activating an acquisition of the signal with the help of a sensor and subsequently the deactivating of the active molecules for example by means of bleaching are carried out. These steps are repeated multiple times and the acquired batch or stack of data taken at different times is reconstructed by means of a computer implemented reconstruction process. For this purpose a segmentation of the data may be carried out initially to identify all molecules. In a further step a fitting of the employed two-dimensional or three-dimensional model functions for the point-spread-function to the identified signals is carried out.

According to an aspect the same point-spread-function is used for the application of the localization microscopy for all fluorescent signals within one object.

For all detected signals of the fluorescent dye molecules one common, theoretical 3D-model function is generated. The 3D-model function is divided in the direction of the optical axis in many layers, and one lateral cross correlation with this 3D model function and a data stack formed by copies of a single image from the acquired image data is carried out. The maxima of the correlation function represent both one object identification and one 3D-localization.

It is thus possible not only to combine the segmentation and localization processes but also to dispense with a relatively computationally intensive fitting of the model function via fit-algorithms such as Levenberg-Marquardt or other modified leased-squares-algorithms. The reconstruction method according to this aspect of the invention is characterized in particular in that it utilizes the fact that all detected signals from the dye molecules are emitted within a single small structure. In such case it is possible to disregard the disturbing differences in the refraction index of the environment, respectively surroundings. One single three-dimensional model function is thereby generated and for example cross-correlated with the data batch, respectively data stack, which is formed by copies of the single images of the acquired image stack (i.e. acquired time series). In the resulting stack it is possible to immediately carry out an identification of the single molecules and simultaneously the position of each molecule in the object or image space from the occurring maxima which describe the similarity of the model function to the signal in one particular layer.

For the optimizing of the object identification and the 3D-localization of the fluorescent dye molecules a threshold method may be used. The threshold-analysis method can be used to optimize the reconstruction method by evaluating only significant maxima. Thus, additional means for quality control of the reconstruction may be obtained.

Instead of cross-correlation a wavelet correlation or similar methods can be used. It is also possible to apply the method of simultaneous segmentation and localization described above in other areas outside the microscopy, which can bring significant economical benefits. In this case the correlation operation may be utilized to decompose the signal in base vectors or components. In the segmentation step, the fact that it is known how the signals are respectively how the weighting of the individual signals should look like (classification, respectively classificators) may be efficiently utilized.

As disclosed in DE 19830596.6, JP 2000502406, U.S. Ser. No. 09/462,435, PCT/EP 02/11343 and WO 2006/127692 A2 the localization precision can be further increased if a structured illumination is also employed for the localization microscopy. The illumination is thereby stationary during the signal acquisition and the fact is exploited that additional information about the potential location of the detected single molecule is obtained, since the molecule is preferably located in a region with a higher intensity.

According to an aspect, a structured illumination, which is moved during the excitation of at least one dye molecule is used also for the application of the localization microscopy. The phase of the modulation is reconstructed in the detected signal from at least one dye molecule, so that the position of at least one molecule associated with a signal relative to at least one fluorescent reference point is determined with a maximal under these condition precision.

The movement of the structured illumination during the signal acquisition results in that the individual molecules can be localized with a maximal under these circumstances precision. It is thereby exploited, that the relative position of the fluorescent molecules to each other or with respect to an additional labeling can be determined from the obtained phase information. The precision with which the phase can be determined lies within a single-digit nanometer range, which corresponds to the achievable localization precision and differs in about one order of magnitude from the conventionally achievable under these circumstances localization precision.

One further factor which limits the precision of the localization microscopy is the used labeling itself. Whereas fluorescent proteins are coexpressed with the protein, which is to be observed, and thus adhere directly to the structure, all other fluorescent molecules must be coupled or bound to the structure via specific linking molecules (for example antibodies or antigenes) or other chemical methods or processes. This coupling, respectively binding over usually greater distances often considerably limits the achievable localization precision, since the position of the molecule which emits the signal relative to the structure under observation is afflicted with some blur or fuzziness. In addition there exist significant problems with non-specific binding, since the binding on the desired region is simply more probable than on some other position. In order to obtain a sufficiently strong signal, however, significantly more dye molecules as needed are introduced into the object under observation, so that with inner structures (for example within the cells) there is a quite strong background, which needs to be dealt with. To overcome this problem is one of the most important objectives of the localization microscopy.

In order to obtain the best results fluorescent proteins or other structurally close molecules can be used as labels. New, genetically modified proteins, which do not exhibit fluorescence in a ground state can be successively, for example photochemically, activated and localized, so that a point-wise reconstruction of the marked structure becomes possible. These specially modified proteins must be introduced into the organism, respectively object to be observed via molecular genetic techniques, which in particular in case of eukaryotic cells is a tedious, expensive and complicated method.

On the other hand, convention fluorescent proteins, which nave not been modified in this way, have been known since the sixties years of the last century. Such proteins have been manifold and successfully employed and are often commercially available in stable expressed cell lines. An utilization of those fluorescent properties for localization microscopy was however up till now not conceivable.

According to an aspect of the invention, non-activatable and non-switchable fluorescent molecules are statistically excited when illuminated with light with intensity lying within intensity range of about 1 kW/cm$^2$ to 1 MW/cm$^2$ of the optical radiation.

Conventional methods of localization microscopy usually employ so called photoswitchable or photoactivatable fluorescent molecules or proteins. Such molecules may be activated/deactivated by illuminating with different characteristical wavelengths. The microscopy techniques based on such special photoswitchable or photoactivatable fluorescent molecules or proteins operate on the principle of absence of fluorescence and differ from the method suggested in the application, which employs illumination with high intensity light. The conventional methods and apparatuses are considerably more complicated than the methods and the apparatuses utilizing high intensity illumination light. In particular, a number of parameters, such as for example the intensities of the plurality of laser sources, or the plurality of filters need to be the simultaneously control and changed during the course of image acquisition. Furthermore, the image acquisition time is usually very long, so that a very high mechanical stability of the overall system is required.

By using high intensity illumination light conventional non-activatable and non-switchable fluorescent molecules may be efficiently utilized for carrying out sub-resolution measurements. Further the whole process may be considerably less complicated and easy to control. Similarly, the data acquisition time may be considerably reduced.

In addition, the utilization of conventional fluorescent proteins is as equally possible with the help of the employed illumination with intensity in the range of about 1 kW/cm$^2$ to 1 MW/cm$^2$ as the optimized activation of their specially modified relatives. Far field acquisitions can be particularly well carried out with the help of those proteins. However, up till now it was believed that such conventional fluorescence proteins are not suitable for localization microscopy methods. The reason for not using up till now such conventional fluorescence proteins, for example GFP (Green Fluorescent Protein) and YFP (Yellow Fluorescent Protein), for the localization microscopy lies in particular in the fact that the intensity region of about 1 kW/cm$^2$ to 1 MW/cm$^2$ was believed to bring only drawbacks both for the wide field microscopy and for the confocal microscopy. In particular in the wide field microscopy the increasing of the intensity was believed to cause a considerably faster bleaching of the probe at no advantages for the achievable resolution, whereas in the confocal microscopy it was believed that an additional intensity (i.e. intensity higher than the above range of about 1 kW/cm$^2$ to about 1 MW/cm$^2$) is required in order to achieve a better signal to noise ratio.

Furthermore, the confocal "one point detection" (single sensor, for example one photodiode) usually employed in a confocal set-up is less or not suitable to visualize the technical effects according to the invention, due to the fact, that all excited molecules within the focal volume contribute simultaneously to the spatially not discriminated signal.

With the help of the method according to an aspect of the present invention established stable labels can be also employed. Thus, thousands of valuable slide preparations or specimens can be analyzed in nanometer range. Furthermore new fluorescence marker such as the so-called "smart-probes" can be utilized for the above described method according to an aspect of the invention. These markers are only active if they are bound to the designated structure and have thus changed their conformation. All of the remaining not bound and not washed away molecules remain thus invisible both for the applied far, respectively wide field technique and for the localization microscopy. Thus, the main advantage is that disturbing background, which exists in the conventional methods, can be substantially eliminated. Furthermore exclusively the cells structure can be reconstructed.

A further aspect of the invention relates to an apparatus for carrying out the method for localizing of single dye molecules in the fluorescence microscopy according to one of the above described aspects, wherein one light microscope with a wide field set-up of the optical illumination path is employed. The apparatus comprises at least one additional optical element, which is built in, respectively positioned within the illumination optical path of the light microscope, so as to enable an adjustment of the determined optimal density of the optical radiation intensity to the and/or within the range of 1 kW/cm$^2$ to 1 MW/cm$^2$.

Accordingly, a conventional wide field illumination can be changed by the employment of at least one suitable optical element such that the intensity of the optical radiation is adjustable to the intensity window or interval of 1 kW/cm$^2$ to 1 MW/cm$^2$. Thus the methods according to any of the aspects of the invention can be enabled, respectively facilitated. With certain dyes or markers it can be advantageous to extend this intensity interval or window in the direction of the higher or lower values.

A further aspect of the present invention relates to an apparatus for carrying out the method for localizing of single dye molecules in the fluorescence microscopy according to any of the above described aspects, wherein one light microscope with confocal set-up of the optical illumination path is employed, wherein at least one additional optical element is built in, respectively positioned within the illumination optical path of the light microscope, so as to enable an adjustment of the determined optimal intensity of the optical radiation to the and/or within range of 1 kW/cm$^2$ to 1 MW/cm$^2$.

In an apparatus according to an aspect of the invention, at least one lens and/or at least one gray filter and/or at least one acoustooptical or electrooptical modulator may be built in, respectively introduced as an additional optical element in the optical illumination path of the light microscope. Particularly easy to implement are thereby for example a single lens or lens systems according or a single gray filter or a gray filter set. A polarization filter provides another a convenient alternative for continuously adjusting or regulating the intensity of the illumination with polarized light sources. Acousto-optical or electro-optical modulators according represent still another alternative. A wide field set-up, which has been modified by the employment of an additional lens as well as a combination from a single lens and a gray filter set has been also successfully tested.

Taken into account that the employment of a very low price laser pointer as an illumination source is similarly possible, it follows that a fully functional far field localization microscopic set-up with some kind of structured illumination integrated into it is also possible for a relatively low price. Low price realizations of the structured illumination can be for example integrated by means of an optical grating or multiray interference. Even without employment of expensive special objectives, main frame or large capacity computers and special sensors the imaging power of such systems within an acceptable time period of under one hour is better than that of conventionally obtainable microscopic systems. In addition, the fact that in the simplest case there is only one degree of freedom available to a user for manipulation (intensity control for example via lens position) assures that such apparatus can be used by everybody even without further knowledge in the field of optic, mechanic or electronic.

Furthermore, at least one additional sensor may be used in at least one additional optical detection path, so as to register additional photons, which would otherwise not reach the first sensor. In this way additional information for the lateral and axial localization may be gathered.

The at least one additional optical detection path may be modified by inserting of at least one additional optical element, so that the data from the additional (second) optical path offer an improved localization precision along the optical axis at the expense of the lateral localization precision. By means of, for example statistical, combination of the single localizations a maximal under these conditions three-dimensional localization precision may be achieved.

The localization of single fluorescent molecules can be additionally optimized by the employment of a second sensor. The additional sensor can be used for example for a phase determination, in particular for the reconstructing of the phase modulation when structured illumination, which is moved during the excitation, is employed for the localization microscopy, in that at least one additional detection optical path as provided.

Similarly it also possible to employ the additional sensor behind the modified additional detection optical path, with which for example an improvement of the axial localization precision can be achieved at the expense of the lateral localization precision. The data collected by all sensors can be for example statistically combined in order to optimize the localization and reconstruction process.

As already described above, according to an aspect there is provided a method and an apparatus for improvement of the localization precision and the achievable object information in the localization microscopy by combining it with far-field techniques with structured illumination, wherein the dye molecules used for the fluorescent marking are excited, subsequent to a convention far-field illumination at intensity below 1 kW/cm$^2$, by an optical radiation having intensity within an intensity range from about 1 kW/cm$^2$ to 1 MW/cm$^2$.

In addition according to a further aspect an improvement of the localization precision is implemented by means of a movement of the structured illumination and an automatic, combined segmentation and localization method. The described methods and apparatuses according to an aspect of the invention broaden the known confocal or wide field illumination set-ups by at least one type of structured illumination and by additional optical elements, which provide the required density of the intensity.

What is claimed is:

1. A method for obtaining a sub-resolution spatial information of a sample labeled with at least one type fluorescent label, said sub-resolution spatial information comprising localization information about positions of fluorescent molecules of the at least one type fluorescent label in at least one spatial direction, comprising the steps:
    acquiring localization image data by employing fluorescence localization microscopy, wherein said localization image data comprises a series of images obtained by
        illuminating a region of interest of the sample with illumination light having intensity in a range of 1 kW/cm$^2$ to 1 MW/cm$^2$,
        detecting by an information acquiring sensor of at least a portion of fluorescent light emitted by at least a portion of the fluorescent molecules of the at least one type fluorescent label upon illumination, thereby obtaining an image of the region of interest;
        repeating the steps of illuminating and detecting of the emitted fluorescent light a plurality of times, thereby obtaining the series of images, each of the images being taken at a different time step;
    processing the acquired localization image data to thereby obtain said localization information about the positions of fluorescent molecules of the at least one type fluorescent label in at least one spatial direction, wherein the step of processing comprises determining in each of the detected images of the series positions of barycenters of the detected fluorescence emission distributions from the single fluorescent molecules of the one or more fluorescent labels in at least one spatial direction.

2. The method according to claim 1, wherein upon illumination, at least a portion of the fluorescent molecules are transferred from a first fluorescent state to a second, reversibly bleached state.

3. The method according to claim 2, wherein upon illumination, at least a portion of the fluorescent molecules of the at least one type fluorescent label are transferred from the first state to the second state and after recovery to the first state to a third, inactive state.

4. The method according to claim 3, wherein the third state is an irreversibly bleached state.

5. The method according to claim 1, wherein the one or more fluorescent labels comprise at least one type of fluorescent proteins, derivatives of fluorescent proteins and modifications of fluorescent proteins.

6. The method according to claim 1, wherein the one or more fluorescent labels comprise at least one of non-protein based fluorescent labels and derivatives of non-protein based fluorescent labels.

7. The method according to claim 1, wherein the one or more fluorescent labels comprise at least one of green fluorescent protein (GFP), derivatives of green fluorescent protein (GFP), cyan fluorescent protein (CFP), yellow fluorescent protein (YFP), OFP, enhanced green fluorescent protein (eGFP), emGFP and enhanced yellow fluorescent protein (eYFP).

8. The method according to claim 1, wherein the one or more fluorescent labels comprise at least one of monomeric red fluorescent protein (mRFP), derivatives of monomeric red fluorescent protein (mRFP), modifications of monomeric red fluorescent protein (mRFP) and mCherry.

9. The method according to claim 1, wherein the one or more fluorescent labels comprise at least one of rhodamin derivatives, Alexa- and attodyes for non-proteins.

10. The method according to claim 1, wherein the one or more fluorescent labels comprise at least one of xanthen derivatives and fluorescein.

11. The method according to claim 1, wherein the one or more fluorescent labels comprise at least one of rhodamin derivatives, Alexa- and attodyes.

12. The method according to claim 1, wherein the one or more fluorescent labels comprise coumarin derivatives.

13. The method according to claim 1, wherein the one or more fluorescent labels comprise cyanin derivatives.

14. The method according to claim 1, wherein the employed fluorescence localization microscope has a confocal set-up of the optical illumination path, a wide field set-up of the optical illumination path, a 4Pi set-up, a STED set-up or STED-4Pi set-up.

15. The method according to claim 1, wherein the used illumination light is monochromatic.

16. The method according to claim 1, wherein a plurality of different types of fluorescent labels are employed and the step of acquiring localization image data of one or more objects in a region of interest by employing fluorescence localization microscopy is carried out separately for each fluorescent label using illumination light with an optimal intensity selected from the range of 1 kW/cm$^2$ to 1 MW/cm$^2$.

17. The method according to claim 1, wherein the step of processing the acquired localization image data comprises fitting of a model function $f(x,y)$ to the acquired fluorescent emission distributions from the single fluorescent molecules in each of the two dimensional images of the time series:

$$f(x, y) = A\exp\left(-\frac{(x_0 - x)^2 + (y_0 - y)^2}{2\sigma^2}\right) + B_0 + B_1(x_0 - x) + B_2(y_0 - y),$$

wherein x and y are cartesian coordinates in an object plane, perpendicular to an optical axis of the microscope;

$x_0$ and $y_0$ are starting parameters for the position, which are determined as a center of a segmented signal;

A is an amplitude of the distribution, and $B_0$, $B_1$, $B_2$ are parameters describing linear background.

18. The method according to claim 1, wherein in the step of acquiring localization image data the one or more objects in the region of interest are illuminated by a structured illumination light.

19. The method according to claim 1, further comprising acquiring additional wide field image data comprising a series of wide field images of the region of interest by employing a wide field fluorescence microscopy using illumination light, which is spatially structured, respectively modulated along an optical axis of the microscope, said acquiring additional wide field image data being obtained by:
  illuminating one or more objects in the region of interest with the structured illumination light;
  detecting a wide field image of the fluorescent light emitted from the fluorescent molecules of the one or more fluorescent labels;
  moving at least one of the object and the structured illumination light in discrete steps along the optical axis and detecting at each step a wide field image of the fluorescent light emitted from the fluorescent molecules, thereby obtaining said series of wide field images of the region of interest,
wherein said step of acquiring additional wide field image data of the one or more objects is carried out before the step of acquiring localization image data.

20. The method of claim 19 further comprising:
  processing the acquired additional wide field image data to obtain at least one set of additional spatial information comprising information about a spatial extension along the optical axis of at least one fluorescently labeled object in the sample and additional spatial information of the positions of the barycenters of the detected fluorescence emission distribution of the single fluorescent molecules in the direction of the optical axis; and
  combining the localization information obtained by the localization microscopy with the additional spatial information obtained by the wide field fluorescence microscopy using structured illumination light.

21. The method of claim 19, further comprising:
  generating a common theoretical three dimensional model function for all detected signals within the one or more objects, wherein said three dimensional model function is divided in plurality of two dimensional layers along the optical axis, and
  performing a lateral cross correlation of the acquired three dimensional image data and said three dimensional model function, wherein the maxima of the correlation function represent both one object identification and one three-dimensional localization.

22. The method of claim 21, further comprising applying a threshold method to the obtained correlation maxima.

23. The method of claim 19 further comprising a step of carrying out a spatial calibration of the structured illumination, wherein the spatial calibration is carried out with the help of at least one fluorescent reference point.

24. The method of claim 19, wherein
  during acquiring additional image data of said one or more objects with wide field fluorescence microscopy using structured illumination light, the one or more objects are illuminated with the structured illumination such, that at least a portion of the fluorescence molecules of the at least one fluorescent label is transferred in an active state and is used for the corresponding far-field observation, whereas a second portion of the fluorescence molecules remains in an inactive state; and
  during the step of acquiring localization image data by employing fluorescence localization microscopy a second portion of the fluorescence molecules is activated by changing of the illumination light intensity of the optical radiation to the one lying within the range of 1 kW/cm$^2$ to 1 MW/cm$^2$, wherein said step of acquiring localization image data by employing fluorescence localization microscopy is carried out on the basis of the second part of the fluorescent molecules.

25. A fluorescence localization microscope for obtaining a sub-resolution spatial information of a sample labeled with at least one type fluorescent label, said sub-resolution spatial information comprising localization information about positions of fluorescent molecules of the at least one type fluorescent label in at least one spatial direction, said microscope comprising:
  an illumination optics defining an optical illumination path, configured to illuminate the one or more objects in a region of interest;
  at least one additional optical element positioned within the optical illumination path of the localization microscope, the at least one additional optical element configured to enable a switching of the intensity of the illumination light to an intensity lying within a range of 1 kW/cm$^2$ to 1 MW/cm$^2$ or an adjustment, respectively regulation of the intensity of the illumination light within the range of 1 kW/cm$^2$ to 1 MW/cm$^2$;
  at least one information acquiring sensor positioned in an optical detection path, configured to detect at least a portion of the emitted fluorescent light, thereby obtaining an image of the illuminated region of interest.

26. The microscope of claim 25, wherein the localization microscope has a confocal set-up of the optical illumination path, a wide field set-up of the optical illumination path, a 4Pi set-up, a STED set-up or STED-4Pi set-up.

27. The microscope of claim 25, wherein the at least one additional optical element comprises one or more of
  at least one lens or a lens system;
  at least one gray filter or a gray filter set;
  at least one polarization filter;
  at least one acoustooptical modulator; and
  at least one electrooptical modulator.

28. The microscope of claim 25, further comprising at least one additional sensor, which is used in at least one additional optical detection path, said additional sensor and said additional optical detection path configured to register at least a portion of the fluorescent light, which does not reach the information acquiring sensor.

29. The microscope of claim 28, further comprising at least one second additional optical element positioned in the least one additional optical detection path.

30. The microscope according to claim 25 comprising furthermore a processing unit, configured to process the acquired localization image data to obtain sub-resolution spatial information of a sample labeled with at least one type fluorescent label, said sub-resolution spatial information comprising localization information about the positions of fluorescent molecules of the at least one type fluorescent label in at least one spatial direction.

* * * * *